United States Patent
Liu et al.

(10) Patent No.: US 9,606,128 B2
(45) Date of Patent: *Mar. 28, 2017

(54) ANTIBODIES AND METHODS FOR DETECTING AND ISOLATING THE COMMON CONJUGATION SITE-SPECIFIC EPITOPES/ANTIGENS

(71) Applicants: Chunli Liu, Baltimore, MD (US); Bingren Hu, Baltimore, MD (US)

(72) Inventors: Chunli Liu, Baltimore, MD (US); Bingren Hu, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/970,376

(22) Filed: Dec. 15, 2015

(65) Prior Publication Data

US 2016/0245823 A1    Aug. 25, 2016

Related U.S. Application Data

(63) Continuation-in-part of application No. 13/312,285, filed on Dec. 6, 2011, now Pat. No. 9,383,367.

(51) Int. Cl.

| | |
|---|---|
| *G01N 33/573* | (2006.01) |
| *G01N 33/68* | (2006.01) |
| *C07K 16/18* | (2006.01) |
| *C12Q 1/34* | (2006.01) |
| *C07K 16/44* | (2006.01) |
| *C12Q 1/37* | (2006.01) |
| *C12Q 1/61* | (2006.01) |

(52) U.S. Cl.
CPC ......... *G01N 33/6878* (2013.01); *C07K 16/18* (2013.01); *C07K 16/44* (2013.01); *C12Q 1/34* (2013.01); *G01N 33/68* (2013.01); *C12Q 1/37* (2013.01); *C12Q 1/61* (2013.01)

(58) Field of Classification Search
CPC .... G01N 33/6878; G01N 33/68; C07K 16/18; C07K 16/44; C12Q 1/34; C12Q 1/61; C12Q 1/37

See application file for complete search history.

(56) References Cited

U.S. PATENT DOCUMENTS 9,383,367 B1 *   7/2016   Liu .................... G01N 33/6878

OTHER PUBLICATIONS

Kirkpatrick et al. Quantitative analysis of in vitro ubiquitinated cyclin B1 reveals compex chain topology. Nature Cell Biol. 2006, vol. 8, No. 7, pp. 700-710 and supporting online material.*

Koivunen et al. Principles of immunochemical techniques used in clinical laboratories. Labmedicine 2006, Vo.37, No. 8, pp. 490-497.*

Wang et al. Analysis of nondegradative protein ubiquitylation with a monoclonal antibody specific for lysine-63-linked polyubiquitin., PNAS 2008, vol. 105, No. 51, pp. 20197-20202.*

* cited by examiner

*Primary Examiner* — Shafiqul Haq

(57) ABSTRACT

This invention discloses the "Artificially Cleaved Epitope (ACE)" methods, antibodies, reagents, immunoassays, immunoaffinity isolation, and kits for all antibody-based applications of designing, detecting, or isolating the common ACE epitopes/antigens in a sample. The ACE methods can detect or isolate epitopes that are either absent or poorly accessible naturally to antibodies, and thus must be specifically and artificially created (free terminals) and/or exposed in a sample for antibody-based applications. The common ACE structures are those that are the common parts of different macromolecule-to-macromolecule conjugation segments. The ACE methods, antibodies, reagents, immunoassays, and kits are useful in research and discovery, diagnostic, and therapeutic applications.

11 Claims, 7 Drawing Sheets

Figure 1A:
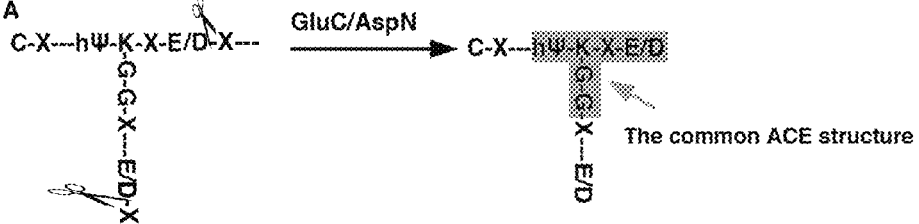

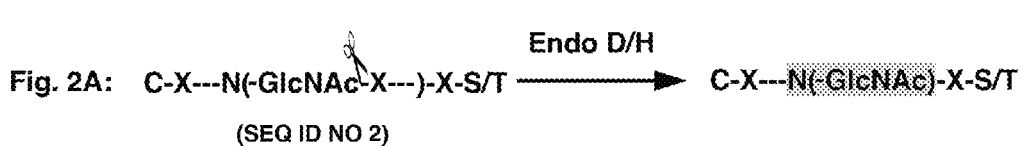
Fig. 2A: C-X---N(-GlcNAc-X---)-X-S/T —Endo D/H→ C-X---N(-GlcNAc)-X-S/T
(SEQ ID NO 2)
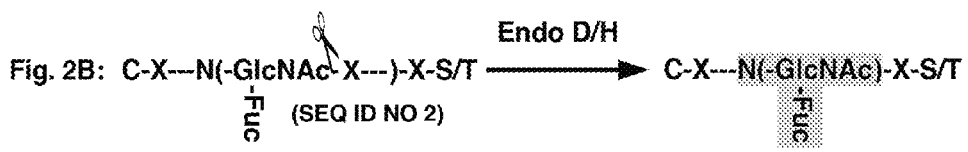
Fig. 2B: C-X---N(-GlcNAc-X---)-X-S/T —Endo D/H→ C-X---N(-GlcNAc)-X-S/T
         -Fuc  (SEQ ID NO 2)                              +Fuc
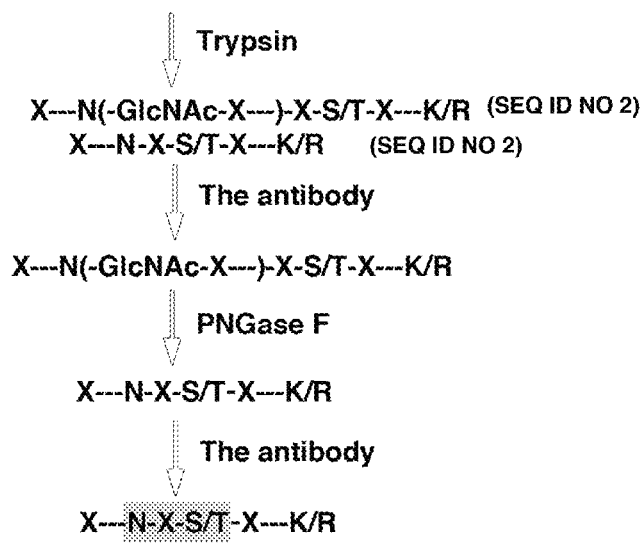
Fig. 2C: K/R-X---N(-GlcNAc-X---)-X-S/T-X---K/R-X---
K/R-X---N-X-S/T-X---K/R-X---
⇩ Trypsin
X---N(-GlcNAc-X---)-X-S/T-X---K/R  (SEQ ID NO 2)
X---N-X-S/T-X---K/R   (SEQ ID NO 2)
⇩ The antibody
X---N(-GlcNAc-X---)-X-S/T-X---K/R
⇩ PNGase F
X---N-X-S/T-X---K/R
⇩ The antibody
X---N-X-S/T-X---K/R

SEQUENCE LISTING

```
<160> NUMBER OF SEQ ID NOS: 7

<210> SEQ ID NO 1
<211> LENGTH: 206
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: Xaa
<222> LOCATION: (102)..(102)
<223> OTHER INFORMATION: Xaa can be any amino acid and preferably a
      hydrophobic amino acid
<220> FEATURE:
<221> NAME/KEY: K
<222> LOCATION: (103)..(103)
<223> OTHER INFORMATION: K is modified via a SUMO or a SUMO fragment
<220> FEATURE:
<221> NAME/KEY: Xaa
<222> LOCATION: (104)..(104)
<223> OTHER INFORMATION: Xaa can be any amino acid
<220> FEATURE:
<221> NAME/KEY: Xaa
<222> LOCATION: (105)..(105)
<223> OTHER INFORMATION: Xaa is either a glutamic acid (E) or an
      aspartic acid (D), and may be absent
<220> FEATURE:
<221> NAME/KEY: Xaa
<222> LOCATION: (106)..(205)
<223> OTHER INFORMATION: Xaa can be any amino acid, and may be less than
      100 or absent
<220> FEATURE:
```

<221> NAME/KEY: Xaa
<222> LOCATION: (206)..(206)
<223> OTHER INFORMATION: Xaa is either a lysine (K) or an arginine (R),
    and may be absent

<400> SEQUENCE: 1

```
Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Lys Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130             135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
    195                 200                 205
```

<210> SEQ ID NO 2
<211> LENGTH: 205
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
    100 or absent
<220> FEATURE:
<221> NAME/KEY: N
<222> LOCATION: (102)..(102)
<223> OTHER INFORMATION: N is modified via an acetylglucosamine or a
    core-fucosylated acetylglucosamine
<220> FEATURE:
<221> NAME/KEY: Xaa
<222> LOCATION: (103)..(103)
<223> OTHER INFORMATION: Xaa can be any amino acid
<220> FEATURE:
<221> NAME/KEY: Xaa
<222> LOCATION: (104)..(104)
<223> OTHER INFORMATION: Xaa is either a serine (S) or a threonine (T),
    and may be absent
<220> FEATURE:
<221> NAME/KEY: Xaa
<222> LOCATION: (105)..(204)
<223> OTHER INFORMATION: Xaa can be any amino acid, and may be less than
    100 or absent

```
<220> FEATURE:
<221> NAME/KEY: Xaa
<222> LOCATION: (205)..(205)
<223> OTHER INFORMATION: Xaa is either a lysine (K) or an arginine (R),
      and may be absent

<400> SEQUENCE: 2

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Asn Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
            195                 200                 205

<210> SEQ ID NO 3
<211> LENGTH: 202
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: Xaa
<222> LOCATION: (102)..(102)
<223> OTHER INFORMATION: Xaa can be any amino acid, and is modified via
      either an ADP-ribose, a P-ribose, or a HAD
<220> FEATURE:
<221> NAME/KEY: Xaa
<222> LOCATION: (103)..(202)
<223> OTHER INFORMATION: Xaa can be any amino acid

<400> SEQUENCE: 3

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
        85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa
        165                 170                 175

Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa
        195                 200

<210> SEQ ID NO 4
<211> LENGTH: 202
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: E
<222> LOCATION: (102)..(102)
<223> OTHER INFORMATION: E is modified via either an ADP-ribose, a
      P-ribose, or a HAD
<220> FEATURE:
<221> NAME/KEY: Xaa
<222> LOCATION: (103)..(202)
<223> OTHER INFORMATION: Xaa can be any amino acid, and may be less than
      100 or absent

<400> SEQUENCE: 4

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
        85                  90                  95

Xaa Xaa Xaa Xaa Xaa Glu Xaa Xaa Xaa Xaa Xaa Xaa Xaa Xaa Xaa
```

-continued

```
            100                 105                 110
Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa
            195                 200

<210> SEQ ID NO 5
<211> LENGTH: 202
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: D
<222> LOCATION: (102)..(102)
<223> OTHER INFORMATION: D is modified via an ADP-ribose, a P-ribose, or
      a HAD
<220> FEATURE:
<221> NAME/KEY: Xaa
<222> LOCATION: (103)..(202)
<223> OTHER INFORMATION: Xaa can be any amino acid, and may be less than
      100 or absent

<400> SEQUENCE: 5

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Asp Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175
```

```
Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa
        195                 200

<210> SEQ ID NO 6
<211> LENGTH: 205
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: R
<222> LOCATION: (102)..(102)
<223> OTHER INFORMATION: R is modified via an ADP-ribose, a P-ribose, or
      a HAD
<220> FEATURE:
<221> NAME/KEY: Xaa
<222> LOCATION: (104)..(104)
<223> OTHER INFORMATION: Xaa can be any amino acid
<220> FEATURE:
<221> NAME/KEY: Xaa
<222> LOCATION: (106)..(205)
<223> OTHER INFORMATION: Xaa can be any amino acid, and may be less than
      100 or absent

<400> SEQUENCE: 6

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Arg Glu Xaa Glu Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

<210> SEQ ID NO 7
```

```
<211> LENGTH: 102
<212> TYPE: PRT
<213> ORGANISM: homo
<220> FEATURE:
<221> NAME/KEY: C
<222> LOCATION: (1)..(1)
<223> OTHER INFORMATION: C is artificially added and may be absent
<220> FEATURE:
<221> NAME/KEY: Xaa
<222> LOCATION: (2)..(101)
<223> OTHER INFORMATION: Xaa can be any amino acid, and may be less than
      100 or absent
<220> FEATURE:
<221> NAME/KEY: Xaa
<222> LOCATION: (102)..(102)
<223> OTHER INFORMATION: Xaa can be any amino acid and is modified via a
      GPI-AM, a GPI-AHM, a GPI-Com, or a GPI-CRD

<400> SEQUENCE: 7

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa
            100
```

ANTIBODIES AND METHODS FOR DETECTING AND ISOLATING THE COMMON CONJUGATION SITE-SPECIFIC EPITOPES/ANTIGENS

CROSS-REFERENCE TO RELATED APPLICATIONS

This application is related to U.S. patent application Ser. No. 13/312,285, filed Dec. 6, 2011, which claims priority to Ser. No. 61/420,354 filed on Dec. 7, 2010.

SEQUENCE LISTING

A sequence listing file: "Sequence_listing_ST25.txt" is included as a separate part within this submission. This ASCII text file is created on Dec. 15, 2015. The file size is 3 kilobytes.

TECHNICAL FIELD

The present description relates to methods, antigens, antibodies, reagents, immunoassays and kits for designing and detecting the common macromolecule-to-macromolecule conjugation site-specific epitope in a sample or a sample preparation, collectively defined as the common ACE methods, and their use thereof.

BACKGROUND OF THE INVENTION

Post-translational conjugation of a protein by another protein, polysaccharide, lipid and nucleic acid, or any combination of the above plays a key role virtually in every aspect of cellular functions. A conjugated molecule is either a monomeric single-molecule or a polymeric macromolecule with either a linear or a branched structure. Macromolecules include, but are not limited to polysaccharides, adenosine diphosphate (ADP)-ribosyls, fatty acids, polynucleotides, glycosylphosphatidylinositol (GPI) anchors, proteins or polypeptides, ubiquitin, small ubiquitin-like modifier (SUMO), neural precursor cell expressed, developmentally down-regulated 8 (NEDD8), interferon-stimulated gene 15 kDa (ISG15), and other ubiquitin-like molecules (UBLs).

Many types of human diseases display abnormal molecular conjugation. For example, abnormal glycosylation occurs in many types of cancers (Mehta and Block, 2008). Ubiquitin-containing conjugates are present in neurodegenerative diseases (Dohm et al., 2008). Telomeric aggregates accumulate in tumor cells (Mai and Garini, 2006). Advanced glycation adducts are found in samples obtained from patients with heart disease and diabetes (Thornalley, 2002; Meerwaldt et al., 2008). Disease-specific macromolecule-to-macromolecule conjugates are present in body fluids such as blood serum or cerebrospinal fluid (CSF), but few reliable methods are currently available to detect a macromolecule-to-macromolecule conjugate in situ or ex situ in a conjugation site-specific manner. Because macromolecule-to-macromolecule conjugation sites are either poorly antigenic or hidden antigens, antibodies to macromolecule-to-macromolecule conjugation sites are extremely difficult to make.

Methods of making antibodies against post-translational modified proteins in the form of a small monomeric molecule, including phosphorylation, acetylation, methylation, and nitrolization, are well established. In comparison to monomeric modification site-specific antibodies, there is no effective method currently available for making polymeric macromolecular conjugation site-specific antibodies. Macromolecular conjugation can be defined as covalent conjugation between two polymeric biomolecules, including, but not limited to, protein glycosylation, lipidation, ADP-ribosylation, ubiquitination, sumoylation, NEDDylation, ISGylation, GPI-anchor, transglutaminase-mediated cross-links, and the like.

In the post-genomic era, our knowledge of macromolecule-to-macromolecule conjugation and its relation to diseases has grown exponentially. For that reason, investigators have devoted extensive efforts to generation of macromolecule-to-macromolecule conjugation site-specific antibodies by conventional antigen design, antibody-making, and antigen detection methods. However, these efforts have been so far proven futile (Matsumoto et al., 2008). Therefore, there is an unmet need of polymeric conjugation site-specific antibodies because they have significant value.

Protein ubiquitination involves many biological processes. There are previous reports of generation of anti-polyubiquitin antibodies. Pirim (1998) reported an anti-polyubiquitin antibody. However, this antibody does not recognize isopeptide bond-branched ubiquitin-to-ubiquitin conjugation, which are dominant forms of cellular ubiquitin conjugates. Rather this antibody recognizes head-to-tail (c- to n-terminal conjugation) poly-ubiquitins.

Fujimuro et al. (2005) reported anti-polyubiquitin monoclonal antibodies named as FK1 and FK2. Both FK1 and FK2 antibodies recognize the polyubiquitin chain. However, there are two fundamental differences between making FK1 and FK2 antibodies, and the antibodies and methods described in the present invention: (i) FK1 and FK2 were made by using regular polyubiquitin antigens; and (ii) FK1 and FK2 cannot recognize the conjugation sites of ubiquitinated proteins (Fujimuro et al., 2005). Therefore, FK1 and FK2 are not conjugation site-specific antibodies, rather than general polyubiquitin antibodies.

There are reports and patents about methods and antibodies to the diglycine-linked lysine structure for profiling of ubiquitinated proteins with liquid chromatography-tandem mass spectrometry (LC-MS/MS) (Peng et al., 2003; Denis et al., 2007; Xu et al., 2010; Kim et al., 2011; U.S. Pat. No. 9,181,326). These antibodies against the diglycine-linked lysine structure were made either with the reaction products between lysine-rich histone III-S protein and t-butyloxycarbonyl-Gly-Gly-N-hydroxysuccinimide (Boc-Gly-Gly-NHS) (Xu et al., 2010), or using the synthetic diglycine-linked peptide library immunogen (U.S. Pat. No. 9,181,326). These antibodies were not produced for detecting hidden antigen in a sample in conventional antibody-based applications such as enzyme-linked immunosorbent assay (ELISA), Western blotting, immunohistochemistry, immunocytochemistry, flow cytometry, and multiplex assay; or combinations thereof, but rather they were developed for the LC-MS/MS profiling of ubiquitinated peptides (Peng et al., 2003; Denis et al., 2007; Xu et al., 2010). In comparison, the inventive ACE methods and antibodies are produced for detecting hidden antigens in a sample in the above-mentioned conventional antibody-based applications. The inventive ACE methods and antibodies do not include those for capturing the diglycine-linked lysine structure in the LC-MS/MS profiling applications.

Matsumoto et al. (2008) generated two linkage-specific antibodies that recognize polyubiquitin chains through lysine 63 (K63) or 48 (K48) linkage (US patent 20070218069A) for the conventional antibody based applications. However, there are several fundamental differences between the method of making these two linkage-specific antibodies and the methods of the present invention. The "antibodies" made by Matsumoto et al. (2008) were not generated by conventional animal immunization methods, rather by a phage display approach of random screening of the ubiquitin conjugation site binders. This phage display approach has advantage to be able to select binding partners from millions of other irrelevant proteins, but these binding partners are "antibody-like" molecules. Also, the phage display approach usually has technical challenges associated with it. For instance, it is acknowledged that the affinity and specificity of binding partners generated by phage display may be suboptimal, relative to conventional immunoglobulin or antibody, and the loss of the original heavy- and light-chain pairings is also a challenge. Perhaps for these reasons, phage display has not been widely used to make "antibodies" reagents (Ward, 2002). In comparison, the present invention uses the Artificially Cleaved Epitope (ACE, see below) strategy for designing and detecting hidden macromolecular conjugation site-specific and linear antigens, which are proven to be effective and reliable.

There are several patented methods for making peptide antibodies. Patent WO 02/25287 describes methods for analysis of proteins by producing a mixture of peptides and contacting the mixture of peptides to filtering agents or antibodies in order to decrease the complexity of a mixture prior to the application of an analytical technique such as mass spectrometry. U.S. Pat. No. 7,460,960 described methods by the use of capture agents or antibodies that interact with the Proteome Epitope Tags (PETs) in a sample. However, these methods cannot be used to design and detect hidden antigens, and they are also principally and profoundly different with the methods of the present invention.

Currently, there are several cleavage site-specific antibodies commercially available. U.S. Pat. No. 7,803,553 described an antibody for detecting an active form of TGF-β1 naturally cleaved in vivo. U.S. Pat. No. 6,762,045 described an antibody to naturally cleaved caspase-3. All currently available cleavage-specific antibodies were developed to detect the naturally occurring cleavage sites in vivo, and cannot be used to detect hidden antigens such as macromolecule-to-macromolecule conjugation sites. In contrast, the present inventive methods are to design and detect "Artificially Cleaved Epitopes (ACEs, see below)" of hidden antigens that are not naturally present or exposed. The inventive ACE methods do not include those for detecting naturally cleaved epitopes in a sample.

Macromolecules other than polypeptides can also be used to generate antibodies successfully, including, but not limited to, antibodies to lipids, nucleic acids, and saccharide. For example, a mouse monoclonal antibody (e.g., CTD110.6) recognizing the single O-linked N-acetylglucosamine (GlcNAc) is commercially available. A mouse antibody (e.g., clone 26-5) to a lipid structure is also reported (Young et al., 1987). However, the common polysaccharide-to-protein and lipid-to-protein conjugation site-specific antibodies described in the present invention are not currently available, most probably because they are hidden antigens which cannot be detected by most conventional antibody-based methods.

SUMMARY OF THE INVENTION

The present invention discloses the "Artificially Cleaved Epitope" or ACE methods, antibodies, reagents, immunoassays, and kits for designing, detecting and isolating hidden antigens, collectively defined as the ACE methods, and their use thereof.

The ACE methods encompass all or part of these steps: (a) Make an ACE antigen by preparing the ACE structure; (b) Make ACE antibody with the ACE antigen by any antibody-making, antibody-like molecule-making methods, and the like; (c) The ACE structure in a sample or a sample preparation is not naturally recognizable by antibody, and thus must be created artificially and precisely either in situ or ex situ by the designated hydrolytic enzyme or chemical agent treatment in a sequence-dependent and residue chemical bond-specific manner; and (d) Detect ACE in situ or ex situ by any antibody-based method in any types of samples or sample preparations. This invention also includes utilities and applications of the ACE methods, antibodies, reagents, immunoassays and kits.

In one embodiment, this invention provides the unique common ACE antigens and the common ACE antigen design methods, wherein the ACE structure must possess one or combinations of these characters: (a) must be antigenic, (b) must be a complete or truncated form of an artificially chemical bond-specific hydrolytic enzyme- or agent-cleaved segment (i.e., the ACE structure); (c) either a branched conjugation site derived from both conjugation moieties, or a linear hidden antigen segment that is folded/buried inside its parent or surrounding structures; (d) must be artificially and specifically created and/or exposed in a sequence-dependent and residue chemical bond-specific manner in a sample or a sample preparation (e.g., Western blot membrane, tissue or cell lysate, tissue section, isolated or culture cell, isolated fraction, any ACE-containing surface, matrices or material, or the like); and (e) the hidden conjugation sites or linear hidden epitopes may be amino acids, peptides, sugar monomers. polymers, lipids/lipid linkers (e.g., ethanolamine), nucleic acids, ADP-ribose, or their combinations.

As mentioned above, most macromolecule-to-macromolecule conjugation sites are hidden antigens. A general hidden macromolecule-to-macromolecule conjugation site-specific ACE structure is: either Ln---L2-L1(-S1-S2---Sm)-L1'-L2'---Lm', or Ln---L2-L1-L1'--L2'---Lm'-(-S1-S2---Sm), wherein the ACE structure is either a branched or a linear segment of an intact macromolecule-to-macromolecule conjugate composed of L and S oligomeric residue chains (e.g., peptides, saccharides, lipids, nucleic acids, ADP-ribosyls, or their conjugates); wherein S1 is covalently conjugated to L1 or Lm' sidechain; wherein Ln, Lm', or Sm are continuously counted from L1, L1' or S1 residues; wherein Ln, Lm', or Sm are not free ends naturally, and have covalent chemical bonds with residues outside of the hidden ACE structure; and wherein said covalent chemical bonds must be artificially and specifically cleaved by specifically designed and chemical bond-specific hydrolysis in a sample or a sample preparation to create and/or expose said hidden ACE structure for antibody binding.

Figure 4:
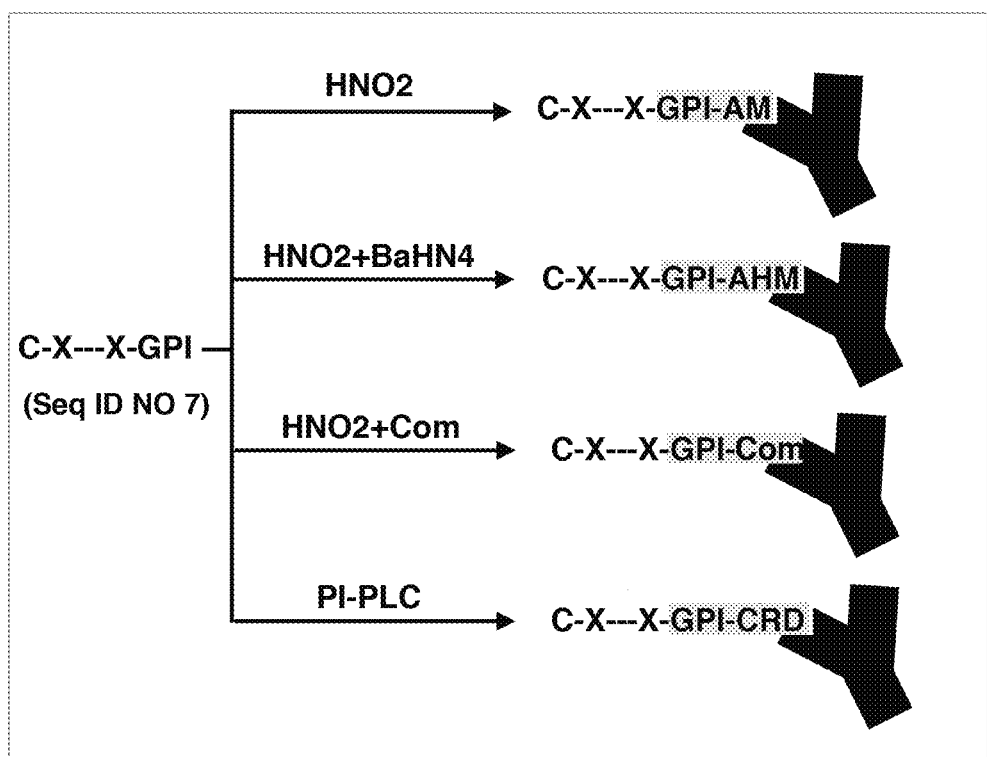
Figure 5:
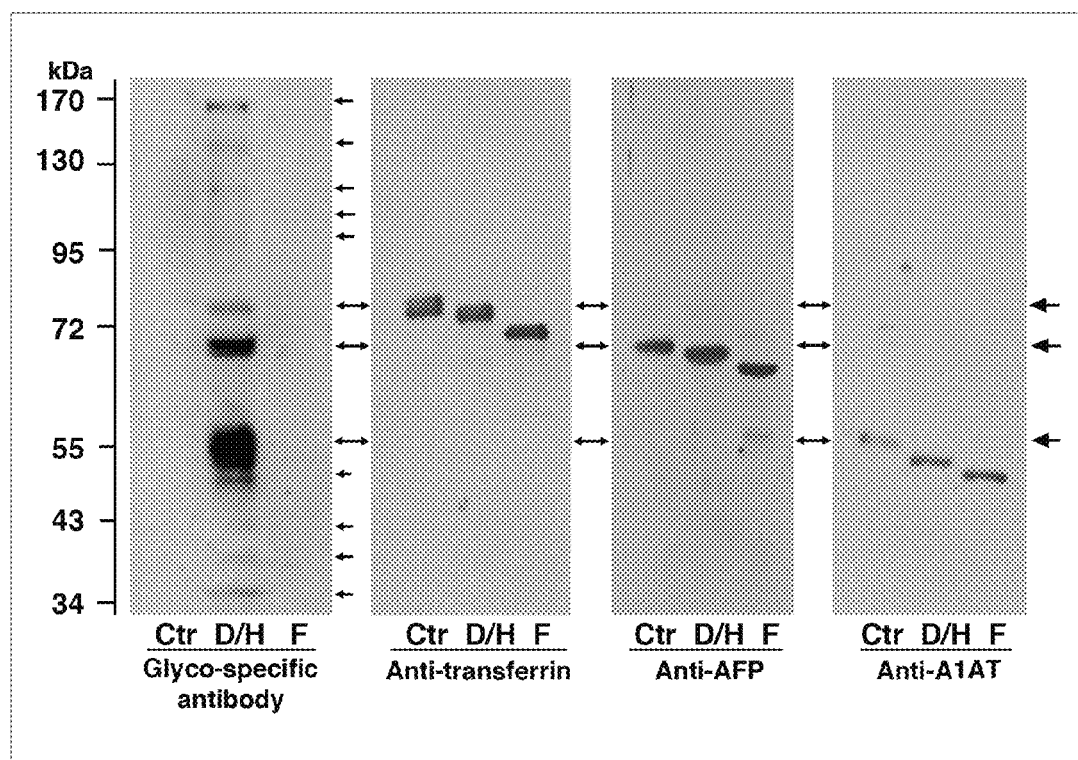
Figure 6:
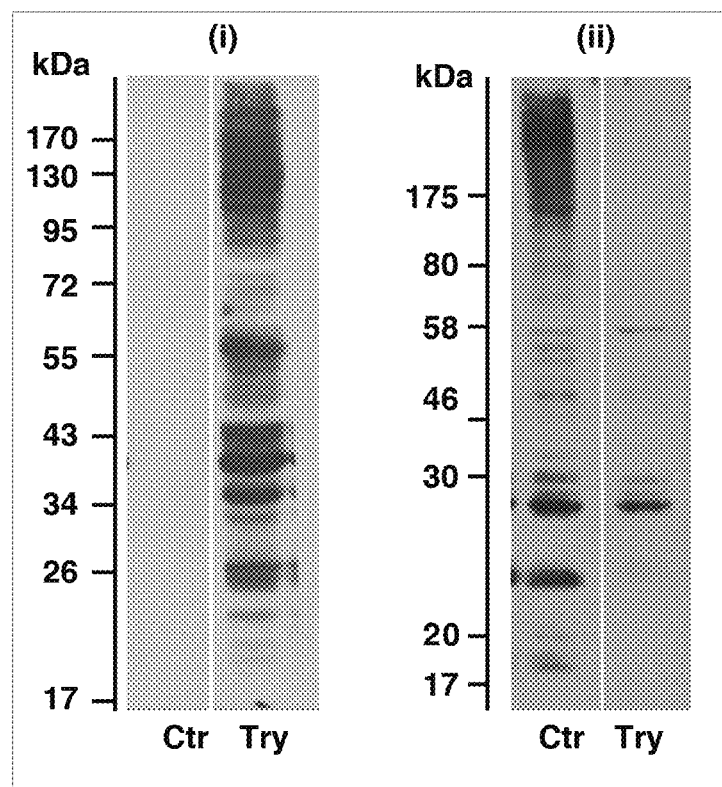
Figure 7:
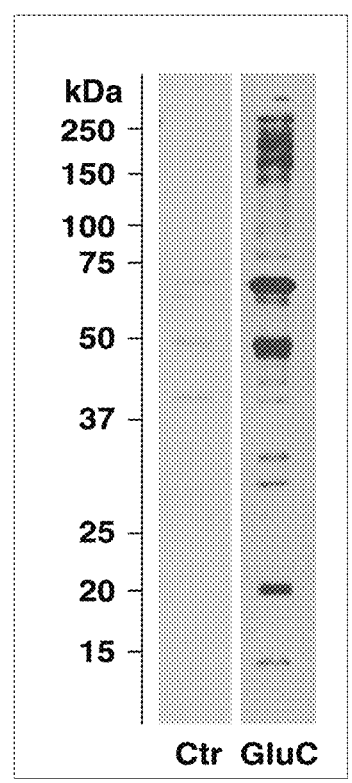

The common ACE epitope of the present invention refers to the same portion or consensus sequence shared by a group of different ACE structures. The antibody specifically binding to the common ACE epitope is referred to as the common ACE antibody. The examples of the common ACE epitopes are shown in FIGS. 1-4. By using the inventive ACE methods, we have generated several common ACE antibodies that specifically bind to their designated common ACE epitopes in a sample or a sample preparation, as shown in FIGS. 5-7.

In another embodiment, the invention provides the common ACE antibodies and methods of using the common ACE epitope or antigen to make antibodies including, but not limited to, a polyclonal antibody, a monoclonal antibody, a bi- or multi-specific antibody, a recombinant antibody, a single-domain antibody, a heavy-chain antibody or $V_HH$ fragment (variable domain of heavy chain antibody), an antibody fragment, a humanized antibody, a binding partner, or an antibody-like molecule.

In a further embodiment, the invention provides antibodies and methods of detecting the common ACE structures in a sample and a sample preparation, wherein the common ACE in a sample is poorly recognizable by antibodies, and thus must be artificially created (with new terminals) and/or exposed specifically and precisely, rather than randomly or accidentally, by residue chemical bond-specific hydrolytic enzymes or agents; wherein said hydrolytic enzymes and agents are specifically selected and should be mostly the same, but may also be different, with the one(s) used for the hydrolysis-guided ACE antigen design; wherein artificially, specifically and precisely creating (new terminals) and/or exposing hidden ACE antigens can be carried out in any samples or sample preparations including, but not limited to, in vivo or in vitro, in whole or part of biological bodies or organisms, in isolated organs or organelles, in tissues or tissue sections (with or without fixation), in isolated or cultured cells, in tissue or cell lysates, in body fluids or cell culture medium, as well as in biochemical assay mixtures, on Western blot or chromatographic membranes or any supporting matrices or surfaces, in chromatographic and centrifuge fractions, in cellular or subcellular fractions, and the likes.

In additional embodiment, the inventive ACE methods can be used to reduce non-specific bindings in all antibody-based applications. This utility is owing to the fact that the chemical bond-specific hydrolysis is able to specifically and precisely create and/or expose the ACE structures, while breaking up other structures/epitopes that are otherwise able to bind to the ACE antibody non-specifically.

The inventive ACE methods, ACE antigens, ACE antibodies, ACE reagents, ACE immunoassays and kits can be used in all antibody-based applications, including, but not limited to, Western blot, immunocytochemistry, immunofluorescence, immunoelectron microscopy, immunoprecipitation, flow cytometry, Enzyme-Linked Immuno-Sorbent Assay (ELISA), peptide array, antibody array, immunoaffinity isolation, enzyme linked immunospot (ELISPOT), immunostaining, immunolabeling, affinity chromatography, mass spectrometry, multiplex assay, and any types of antibody-based assays or combinations thereof.

The inventive ACE methods, antigens, antibodies, reagents, immunoassays and kits can be employed in a number of areas, including, but not limited to: (a) determination of specific conjugation sites and their common or consensus sequences, (b) monitoring changes in the common molecule-to-molecule conjugation sites in vivo and in vitro, (c) diagnosis of diseases, (d) determination of molecular conjugation enzyme and chemical agent activities, (e) determination of molecular conjugation enzyme modulator or cofactor activities, (f) development of therapeutic agents for treatment of diseases, and (g) the like.

Examples of diagnosing diseases with the common ACE methods, antibodies, reagents, immunoassays, and kits may include, but are not limited to: (a) cancers by assaying the common cancer-specific core-fucosylated epitope/antigen; (b) neurological, neurodegenerative, and conformational diseases; and (c) heart disease, muscle diseases (e.g., dermatomyositis), alcoholic liver disease, stroke and diabetes by assaying the common ACE structures, and (c) the like.

The ACE methods, antibodies and reagents can be used in therapeutic applications including, but not limited to, those related to abnormal macromolecule-to-macromolecule conjugation.

The ACE methods, antibodies, reagents, immunoassays, and kits can be used in the area of biomaterials such as collagen-like biomaterials.

The ACE methods, antibodies, reagents, and immunoassays can be assembled to kits for research, diagnostic and therapeutic applications.

BRIEF DESCRIPTION OF THE DRAWINGS

In the brief description of FIGS. 1-7, all the common ACE epitopes or antigens below are derived from either the branched Ln---L2-L1(-S1-S2---Sm)-L1'-L2'---Lm' or Ln---L2-L1-L1'-L2'---Lm'(-S1-S2---Sm) ACE structures as described above in the section (SUMMARY OF THE INVENTION). In exemplary ACE structures described in this invention, the single capital letters represent one-letter standard amino acid abbreviations. For instance, G=glycine, K=lysine, Q=glutamine, etc. KLH all together is the abbreviation for Keyhole Limpet Hemocyanin, which is one of the most commonly used immunogenic carriers for antibody production. The dash "-" represents covalent chemical bond conjugation. The peptide sequence inside the brackets "[ ]" or parentheses "( )" often represents the conjugated monomer or oligomer including, but not limited to amino acid(s)/peptide(s), lipid(s), saccharide(s), ADP-ribose, nucleic acid(s), and the likes. GPI to -protein conjugation is an example of the linear covalent conjugation of GPI to the C-terminal amino acid sidechain of a protein. X in the ACE structures represent any residue or a portion of it, including but not limited to an aminoacid, a saccharide, a lipid, a nucleic acid, a ADP-ribose, a GPI, and the like. X--- represents 0-100 different residues in a polymer. Furthermore, a conjugation site-specific hidden antigen can be designed by the ACE methods in different ways depending on which hydrolytic enzyme(s) or agent(s) will be used for detection or isolation of the ACE structures in a sample.

The following are exemplary designs of the common ACE structures, wherein hΨ and Ψ are interchangeable and is a hydrophobic residue such as alanine (A), valine (V), leucine (L), isoleucine (I), methionine (M) and phenylalanine (F), wherein the X residue can be either a natural amino acid or non-natural amino acid. In the common ACE structures, it is preferable to use non-natural or unnatural amino acids in the X positions in order to avoid the cross-reaction with the amino acid sequence of a particular protein sequence in a sample or sample preparation. Examples of non-natural amino acids include, but not limited to: d-amino acids, homo (h) amino acids, N-methyl amino acids, alpha-methyl amino acids, beta (homo or h) amino acids, gamma amino acids, helix/turn stabilizing motifs, and backbone modifications (e.g. peptoids).

The removal of SUMO from its conjugated proteins is mediated by a family of proteases known as ubiquitin-like-protein-specific proteases (Ulps) in yeast and sentrin-specific proteases (SENPs) in mammals. They are also commonly referred to as deSUMOylation enzymes.

Adenosine diphosphate (ADP)-ribosylation is a reversible posttranslational modification of proteins wherein a single unit (mono-ADP-ribosylation) or a polymeric chain (poly-ADP-ribosylation) of ADP-ribose residue(s) is conjugated to a protein either by mono-ADP-ribosyltransferases or poly-ADP-ribosyltransferases (PARPs). ADP-ribosylation is involved in many cellular processes, including, but not limited to, cell signaling, DNA repair, gene regulation, translation, protein degradation, inflammation, and cell death. Improper ADP-ribosylation has been implicated in diseases including, but not limited to, cancers, diabetes, neurodegenerative disorders, stroke, and heart failure. Some bacterial compounds such as cholera toxin, diphtheria toxin, pertussis toxin, heat-labile enterotoxin of E. Coli, exotoxin A, C3 toxin and many others, exert their toxicities via ADP-ribosylation of proteins such as GTP-binding proteins (e.g., Rho, Ras, Gi, Go, and Gt) and ribosomal elongation factor EF-2. Because of importance, many therapeutic PARP inhibitors have been developed. Therefore, development methods and antibodies for antibody-based detection or isolation of ADP ribosylated proteins can create significant value.

The enrichment of mono-ADP-ribosylated proteins or peptides is a critical determinant of successfully identifying ADP-ribosylated proteins in a sample by e.g., mass spectrometry (MS) analysis (Daniels et al., 2015). Currently, the mostly used is an immunoaffinity isolation of poly(ADP-ribose) polymers longer than 20 subunits with the 10H antibody. However, these 10H antibody-based enrichment methods are mainly for poly(ADP-ribose) polymers and cannot differentiate mono- from poly-ADP-ribosylated proteins. The pyrophosphatases, e.g., snake venom phosphodiesterase (SVP) or NudT16), and poly(ADP-ribose) glycohydrolase (PARG) and ADP-ribosylhydrolase 3 (ARH3) have been used efficiently to convert a poly-ADP-ribosylated protein or peptide to a mono-ADP-ribosylated protein or peptide. Because mono-ADP-ribosylated peptide has a 541.06 Dalton mass shift, isolation or enrichment of mono-ADP-ribosylated protein or peptide will have significant advantage over the 10H antibody-based enrichment of poly-(ADP-ribose) polymers (Daniels et al., 2015). However, antibody specifically binds to mono-ADP-ribosylated protein or peptide is not currently available. The inventive ACE methods and antibodies can be used to isolate mono-ADP-ribosylated protein or peptide. Furthermore, a hydrolytic agent hydroxylamine can be used to cleave the ADP-ribosyl moiety from acidic (glutamic and aspartic) amino acid residues. The resultant hydroxamic acid derivative has a mass shift of 15.01 Daltons, which is easily distinguishable by MS for identifying acidic ADP-ribosylation sites and proteins (Zhang et al., 2013). The IMAC or TiO2 materials have been used to isolate ADP-ribosylated peptide, but the efficiency is significantly lower than antibody-based methods (Laing et al., 2011). However, the methods and antibodies for specifically isolating these hydrolyzed moieties are not currently available. Furthermore, the distinction between mono- and poly-ADP-ribosylated proteins is critical for understanding the role of ADP-ribosylation. This invention provides methods and antibodies for specifically isolating these hydrolyzed moieties, and can also be used to separate mono- from poly-ADP-ribosylated proteins or peptides (see FIG. 3 below). Therefore, the inventive ACE methods and antibodies have distinctive and significant advantage relative to the methods described in the prior art.

Many cell surface proteins are tethered to the membrane by GPI-anchors. The GPI-anchor structure can be selectively and specifically cleaved by several hydrolytic enzymes and agents. As shown in FIG. 4, nitrous acid treatment of a GPI anchor-to-protein conjugate-containing sample at room temperature (pH 4.0) can specifically and selectively cleave the glucosamine-inositol glycosidic bond to create an ACE structure on the GPI glycan with a free reducing terminus in the form of 2,5-anhydromannose (referred to as GPI-AM hereafter). This terminus can further be reduced to 2,5-anhydromannitol (AHM) by sodium borotritide (NaBH4) (referred to as GPI-AHM hereafter), thus providing an opportunity to introduce an isotopic hydrogen for MS analysis. This terminus can also be attached to the reactive compound (Com) such as 2-aminobenzamide (referred to as GPI-Com hereafter). Therefore, the common ACE structures with GPI-AM, GPI-AHM and GPI-Com conjugations can be used to generate the common ACE antibodies. Furthermore, GPI anchor can be specifically cleaved with phospholipase C (PLC) or D (PLD). GPI anchor cleaved by PLC creates a structure known as cross-reacting determinant (CRD) (referred to as GPI-CRD hereafter) (Zamze et al., 1988). The present invention provides the ACE methods for detecting these common ACE structures, because these ACE structures can be artificially created in a sample or a sample preparation and detected or isolated by any antibody-based methods such as Western blotting and immunohistochemistry.

FIG. 1 (A-D). Flow diagrams of antibody detecting or isolating the common ACE epitopes of sumoylated proteins.

FIG. 1A. A method of detecting or isolating the common sumoylation site-specific ACE epitope. Left (from the arrow): A branched polypeptide or protein sequence is composed of -X---hΨ-K-X-E/D-X--- moiety derived from a protein, and -G-G-X---E/D-X--- moiety from a SUMO molecule, wherein the branched structure is presented as C-X---hΨ-K(-G-G-X---E/D-X---)-X-E/D-X---, wherein the first G of the -G-G-X---E/D-X--- in parentheses is covalently conjugated to the K of the X---ΨT-K-X-E/D-X--- via an isopeptide or a chemical bond, wherein C is a cysteine residue either naturally present or artificially added for conjugation to an immunogenic carrier such as KLH, wherein (hΨ) is any amino acid [including those of a non-nature hydrophobic D- or homo-amino acid such as beta-(homo)alanine, beta-(homo)valine, beta-(homo)lucine, beta-(homo)isolucine, or beta-(homo)phenylalanine], wherein X is any amino acid (including those of a non-nature hydrophilic homo amino acid such as beta-homoproline, beta-homoserine, beta-homothreonine, or beta-homoasparagine), wherein X--- represents 0-100 different X residues; wherein different X--- residues are arranged in any random or scrambled order. Right (from the arrow): After hydrolysis with endoproteinase GluC and/or endoproteinase AspN either in situ or ex situ in a sample, the ACE structure -hΨ-K(-G-G-X---E/D)-X-E/D is artificially created in the sample. The antibody can be made with an immunogen containing the common ACE structure (shade area), wherein the antibody specifically binds the common ACE structure or the common ACE structure with the consensus motif, but the antibody binding is independent of the X amino acid residues. Therefore, the common ACE structure in the sample can be specifically detected or isolated with the antibody by all antibody-based methods.

Figure 1B:
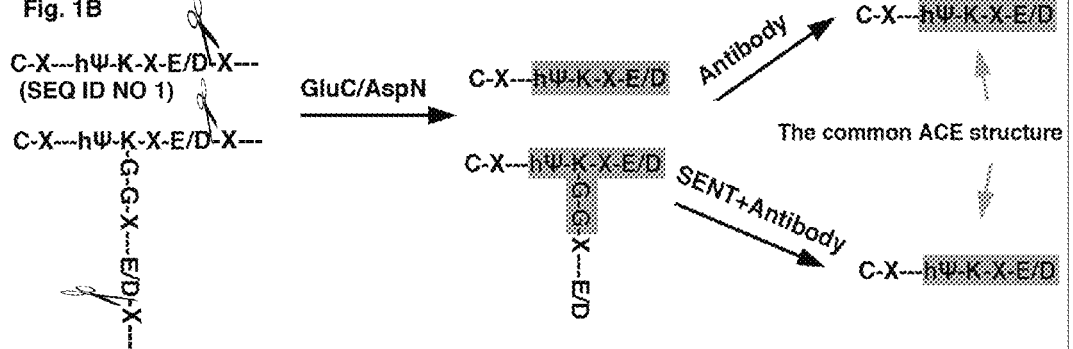

FIG. 1B. Another method of detecting or isolating the common sumoylation ACE epitope. Left: upper C-X---hΨ-K-X-D/E-X--- (SEQ ID NO 1) is the same as in FIG. 1A-left without the branched sequence in the parentheses (-G-G-X---E/D-X---), and lower is the same structure as in FIG. 1A-left. Middle: After GluC and/or AspN treatment of a sample, both X---hΨ-K-X-E/D and X---hΨ-P-K(-G-G-X---E/D)-X-E/D ACE structures are created in the sample. Right: The antibody can be made with immunogens containing the common ACE structure hΨ-K-K-X-E/D (shade area). The antibody can be used to remove the non-sumoylated peptides with the hΨ-K-X-E/D structure from the sample. The sample will be further treated with a desumoylation enzyme (e.g., SENT), which converts X---hΨ-K(-G-

G-X---E/D)-X-E/D to X---hΨ-K-X-E/D. Therefore, the newly converted X---hΨ-K-X-E/D peptides in the sample can be specifically detected or isolated with the antibody by all antibody-based methods.

Figure 1C:
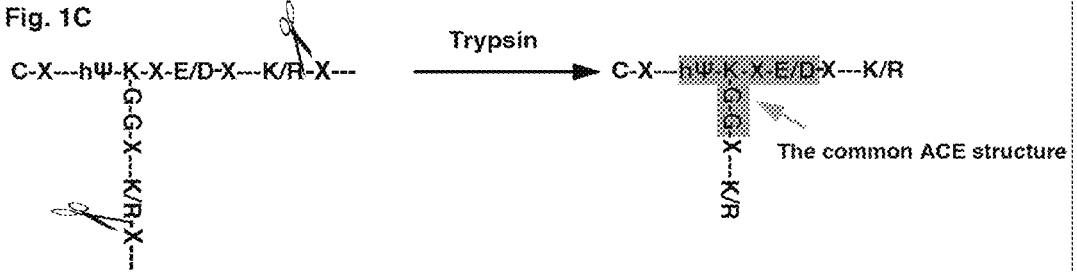

FIG. 1C. A trypsin-digestion method of detecting or isolating the common sumoylation site-specific ACE epitope. Left: A branched polypeptide or protein is composed of -X---hΨ-K-X-E/D-X---K/R-X--- moiety derived from a protein, and -G-G-X---E/D-X---K/R-X---moiety from a SUMO molecule, wherein the branched structure is presented as C-X---hΨ-K(-G-G-X---E/D-X---K/R-X---)-X-E/D-X---K/R-X---, wherein the first G of the -G-G-X---E/D-X---K/R-X--- in parentheses is covalently conjugated to the K of the X---hΨ-K-X-E/D-X---via an isopeptide or a chemical bond, wherein C, hΨ, X, and X--- residues(s) are the same as in FIG. 1A, and wherein K/R are lysine or arginine residues. Right: The common ACE structure hΨ-K(-G-G)-X-E/D (shade area). The common ACE antibody can be made with an immunogen containing the common ACE structure hΨ-K(-G-G)-X-E/D. After treatment of a sample with trypsin to expose the common ACE structure either in situ or ex situ, the common ACE epitopes can be specifically detected or isolated in the sample with the ACE antibody by all antibody-based methods.

Figure 1D:
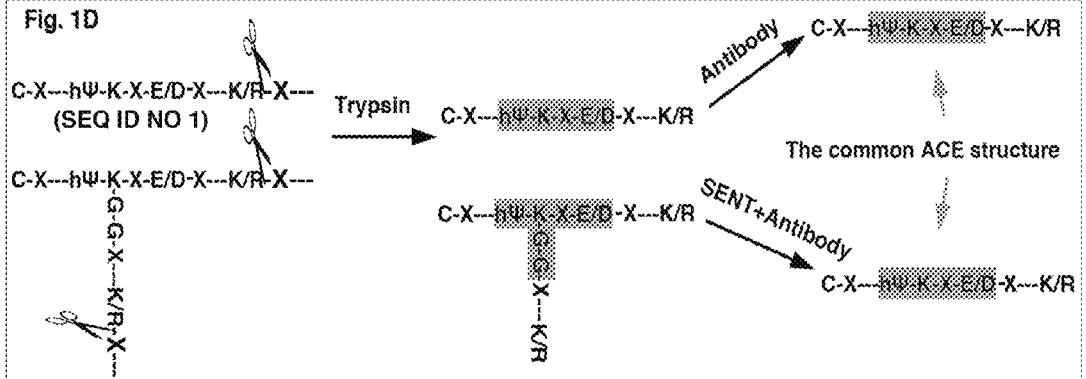

FIG. 1D. Another trypsin-digestion method of detecting or isolating the common sumoylation site-specific ACE epitope. Left: upper C-X---hΨ-K-X-D/E-X---K/R-X--- (SEQ ID NO 1) is the same as in FIG. 1C-left without the branched sequence in the parentheses (-G-G-X---E/D-X---K/R-X---), and lower is the same structure as in FIG. 1C-left. Middle: After trypsin treatment of a sample, both -X---hΨ-K-X-E/D-X---K/R and -X---hΨ-K(-G-G-X---E/D-X---K/R)-X-E/D-X---K/R ACE structures are created in the sample. Right: The common ACE antibody specifically recognizes the common motif in the hΨ-K-X-E/D-X---K/R but the antibody binding is independent of hΨ and X residue. The antibody can be made with a peptide immunogen containing the common ACE structures hΨ-K-X-E/D. The antibody can be used first to remove the non-sumoylated peptide -X---ΨT-K-X-E/D-X---K/R structure from the sample. The sample can be further treated with a desumoylation enzyme (SENT), which converts X---hΨ-K(-G-G-X---E/DX---K/R)-X-E/D-X---K/R to X---hΨ-K-X-E/D-X---K/R. Therefore, the newly converted X---hΨ-K-X-E/D-X---K/R peptide can then be specifically detected or isolated from the sample with the antibody by antibody-based methods.

FIG. 2 (A-C). Flow diagrams of antibody detecting or isolating the common ACE epitopes of glycosylated proteins.

FIG. 2A. Left: A glycosylated protein is composed of a protein moiety -X---N-X-S/T- and a polysaccharide moiety -GlcNAc-X---, wherein the glycosylated protein is presented as C-X---N(-GlcNAc-X---)-X-S/T- (SEQ ID NO 2), wherein GlcNAc is a N-acetyl-D-glucosamine, wherein N is an asparagine, wherein the first GlcNAc of the -GlcNAc-X--- in the parentheses is covalently conjugated to the N of the -X---N-X-S/T-, wherein C is a cysteine residue either artificially added or naturally present in the structure for conjugation to an immunogenic carrier such as KLH, wherein S/T denotes either serine (S) or threonine (T) residue, wherein X is a monosaccharide or amino acid residue (including those of non-nature hydrophilic homo amino acids such as beta-homoproline, beta-homoserine, beta-homothreonine, or beta-homoasparagine), and wherein X--- represents 0-100 different X aminoacid or saccharide residues. Right: The common ACE structures -N(-GlcNAc)- (shade area) and -N(-GlcNAc)-X-S/T. The common ACE antibody can be made with an immunogen containing the common ACE structure N(-GlcNAc) or N(-GlcNAc)-X-S/T, wherein the antibody specifically binds to the common ACE structures, but the antibody binding is independent of X residues. After treatment of a sample with an endoglycosidase (e.g., D, F, F1, F2 or H) or combinations of endoglycosidases (e.g., Endo D/H) to create and/or expose the common ACE structure either in situ or ex situ, the common ACE epitope in the sample can be specifically detected or isolated with the corresponding ACE antibody by all antibody-based methods.

FIG. 2B. Left: A glycosylated protein is composed of a protein moiety -X---N-X-S/T- and a polysaccharide moiety -(GlcNAc-Fuc)-X---, wherein the glycosylated protein is presented as C-X---N[-(GlcNAc-Fuc)-X---]-X-S/T- (SEQ ID NO 2), wherein the GlcNAc of the -(GlcNAc-Fuc)-X--- in the parentheses is conjugated to the N, wherein GlcNAc, N, X, S, T, and X--- are the same as in FIG. 2A, wherein Fuc is a fucose, and wherein (GlcNAc-Fuc) represents the Fuc conjugation to the GlcNAc via an alpha 1,6 linkage or any other linkage. Right: The common ACE structures -N[-(GlcNAc-Fuc)]- (shade area) or -N[-(GlcNAc-Fuc)]-X-S/T. The common ACE antibody can be made with an immunogen containing the common ACE structure -N[-(GlcNAc-Fuc)]- or -N[-(GlcNAc-Fuc)]-X-S/T, the antibody specifically binds to the common ACE structures, but the antibody binding is independent of C and X residues in the structure C-X---N[-(GlcNAc-Fuc)-X---]-X-S/T-. After treatment of a sample with an endoglycosidase (e.g., D, F, F1, F2 or H) or combinations of endoglycosidases (e.g., Endo D/H) to create and/or expose the common ACE structure either in situ or ex situ, the common ACE epitope can be specifically detected or isolated in the samples with the corresponding ACE antibody by all antibody-based methods.

FIG. 2C. Flowchart of antibody detecting or isolating the common ACE epitope of glycosylated proteins consisting of at least one of the following steps. Step 1: A glycosylated protein is presented as ---K/R-X---N(-GlcNAc-X---)-X-S/T-X---K/R-X--- and non-glycosylated protein as ---K/R-X---N-X-S/T-X---K/R-X---, wherein residues and the conjugation are the same as those described in FIG. 2A. Step 2: After trypsin treatment of a sample, the peptide segments with structures of -N(-GlcNAc)-X-S/T- (SEQ ID NO 2) or -N-X-S/T- (SEQ ID NO 2) are exposed in the sample. Step 3: The common ACE antibody can be made with an immunogen containing the common ACE structure N-X-S/T motif, wherein the common ACE antibody specifically binds only to the consensus N-X-S/T motif, wherein the antibody binding is independent of X or any other residues, and wherein the antibody does not recognize the structure of -N(GlcNAc-X---)-X-S/T. The antibody can be used to remove the structures containing N-X-S/T motif from a sample while structures with N(-GlcNAc-X---)-X-S/T structure remain in the sample. Step 4: After further treatment of the sample with N-glycosidase F (also known as PNGase F) or combinations of PNGase with endoglycosidases, the structures containing N(-GlcNAc-X---)-X-S/T motif are changed to the structures with the N-X-S/T motif in the sample. Step 5: Therefore, the common ACE antibody to the common ACE structure N-X-S/T (shade area) can be used to specifically detect or isolate the newly created X-N-X-S/T-X---K/R structures by antibody-based methods.

Figure 3:
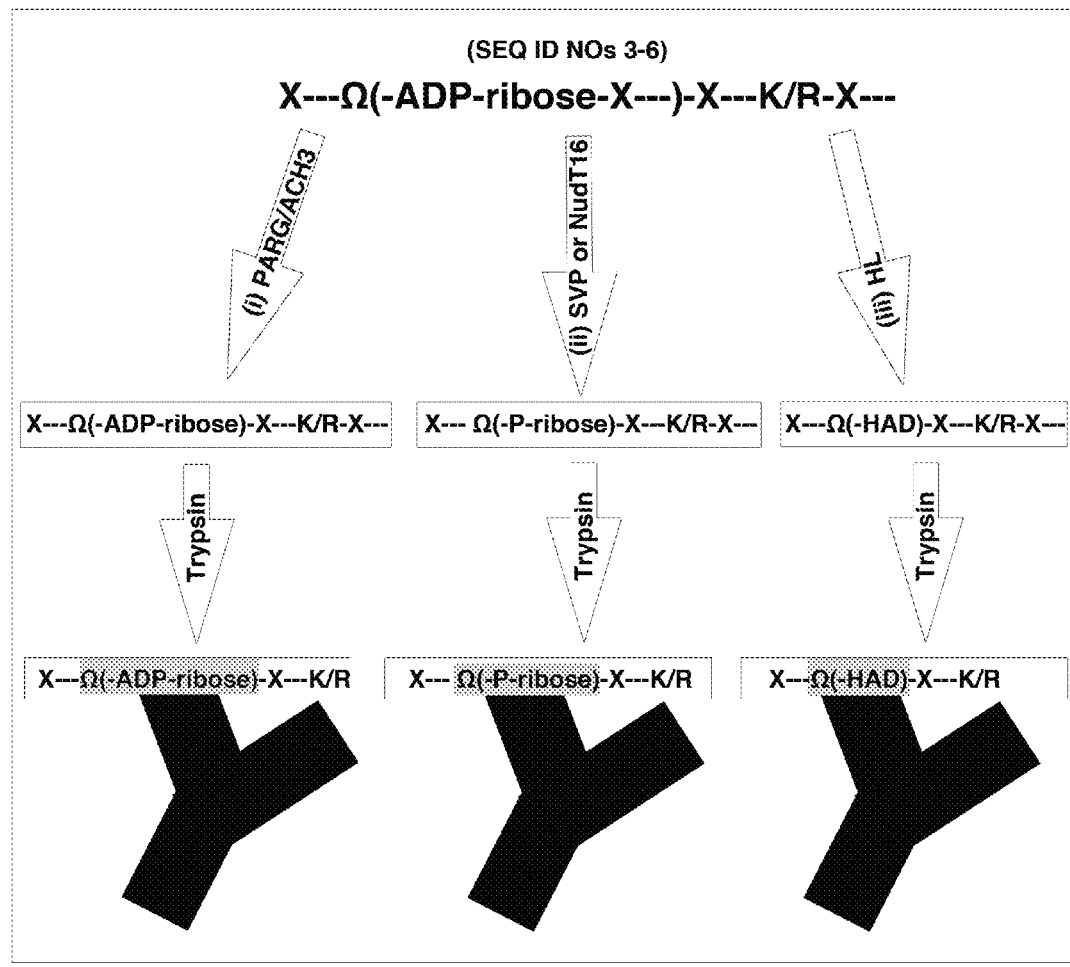

FIG. 3. Flowchart of antibody detecting or isolating the common ACE epitopes of poly-ADP-ribose-proteins consisting of at least one of the following steps. Step 1: The structure X---Ω(-ADP-ribose-X---)-X---K/R-X--- represents a poly-ADP-ribose-protein or -peptide, wherein Ω is any ADP-ribosylated aminoacid residue, and wherein X, K, R are the same as in FIGS. 1-2. Step 2: Treatment of a sample with: (i) PARG/ARH3 creates X---Ω(-ADP-ribose)-X---K/R-X--- containing a unique common ADP-ribosylated ACE structure -Ω(-ADP-ribose)-; (ii) SVP or NudT16 creates X---Ω(-P-ribose)-X---K/R-X--- containing another unique common ADP-ribosylated ACE structure -Ω(-P-ribose)-, wherein P is a phosphate residue; and (iii) hydroxylamine (HL) creates X---Ω(-HAD)-X---K/R-X--- containing the third unique common ADP-ribosylated ACE structure -Ω(-HAD)-, wherein HAD is a hydroxamic acid derivative. Further trypsin treatment of the samples creates X---Ω(-ADP-ribose)-X---K/R, X---Ω(-P-ribose)-X---K/R, and X---Ω(-HAD)-X---K/R ACE structures, respectively. Step 3: The common ADP-ribosylated ACE antibodies to the corresponding common ACE epitopes (shade area) of the structures -Ω(-ADP-ribose)-X---; -Ω(-P-ribose)-X---, or -Ω(-HAD)-X---, can be made with immunogens containing the corresponding common ACE structures, wherein the antibody specifically binds the common ACE structures, and wherein the antibody binding is independent of X amino acid or the rest of poly-ADP-ribose residues.

FIG. 4. Flowchart of antibody detecting or isolating the common ACE epitopes of GPI-anchored proteins consisting of at least one of the following steps. Step 1: C-X---X-GPI (SEQ ID NO 7) is a GPI-anchored peptide derived from a GPI-anchored protein, wherein C, X- and X--- are the same as those presented in FIG. 1, wherein GPI is conjugated to the C-terminal X aminoacid residue. Step 2: Treatment of a sample with: (i) nitrous acid ($HNO_2$) creates an common GPI ACE structure with free reducing terminus in the form of 2,5-anhydromannose (referred to as X---X-GPI-AM hereafter); (ii) $HNO_2$+sodium borotritide (NaBH4) creates another common GPI ACE structure with 2,5-anhydromannitol terminal (referred to as X---X-GPI-AHM hereafter); or (iii) phospholipase C (e.g., phosphoinositide phospholipase C=PI-PLC) creates the third common GPI ACE structure known as the cross-reacting determinant (CRD) (referred to as X---X-GPI-CRD hereafter). Step 3: The common ACE antibodies can be made with immunogens containing the corresponding common GPI ACE structures X-GPI-AM, X-GPI-AHM, or X-GPI-CRD, wherein antibody specifically binds to the common ACE structures, and wherein the antibody binding is independent of the other X residues. The antibody can be used to specifically detect or isolate these common ACE structures in the sample by any antibody-based methods.

FIG. 5. Western blot application of the common glycoform-specific antibody. Samples from the cell culture media were treated with a non-enzyme solution (Ctr), a mixture of endo-D/H, or a general PNGase-F (F) solution. Samples were then subjected to immunoblot analysis. Immunoblot membranes were labeled with: the common ACE antibody that recognizes the common ACE structure [-N(-GlcNAc)-] of all glycosylated proteins (the first blot from the left), a pan or total anti-transferrin antibody (the second blot from the left), a pan or total anti-AFP antibody (the third blot from the left), and a pan or total anti-alpha-1-antitrypsin (A1AT) antibody (the fourth blot from the left). As shown in the first blot labeled with the Glyco-specific antibody, the common ACE antibody does not recognize the polyglycosylated proteins (lane-1, Ctr=without deglycosylation), but after endo D/H treatment of the sample to leave only one GlcNAc on proteins (Lane-2, D/H), the antibody specifically binds to the mono-glycosylated proteins, and furthermore the antibody does not recognize totally deglycosylated proteins after PNGase-F (F) treatment to removes all N-glycan from proteins in the sample (lane-3, F). In comparison, the pan or total antibodies detect all three forms (polyglycosylated, monoglycosylated and non-glycosylated) of the proteins in the samples, respectively, as shown in the $2^{nd}$-$4^{th}$ immunoblots. This is because these pan or total antibodies bind non-glycosylation segments of the proteins and thus they are independent of deglycosylation treatment. The arrows point to the corresponding glycosylated and deglycosylated protein positions among different blots. Molecular weight standards are indicated on the left.

FIG. 6. Western blotting of the common ACE structure of ubiquitin-to-protein conjugation sites in a sample. The cell lysate samples were subjected to immunoblot analysis. Immunoblot membranes (i) and (ii) were blocked with BSA and treated with a non-enzyme solution as a control (lane 1=Ctr), or a trypsin solution (lane 2=Try) to create the ACE structure. After washing and blocking of non-specific binding, the immunoblot membranes were labeled with: (i) the common ACE antibody, and (ii) a pan or total ubiquitin antibody (this pan or total ubiquitin antibody recognizes the ubiquitin moiety of ubiquitinated proteins). As shown in immunoblot (i) lane-1 (Ctr), without the hydrolysis treatment of the sample preparation, the common ACE antibody cannot detect the common ubiquitination sites because the ACE structures were not created by the hydrolysis treatment. In comparison, as shown in immunoblot (i) lane 2 (Try=trypsin), with the hydrolysis (trypsin) treatment, the common ACE antibody can detect the common ubiquitination sites of all ubiquitinated proteins in the sample because the common ACE structure from all ubiquitinated proteins was created by the hydrolysis treatment. On the contrary, as shown in immunoblot (ii) lane 1 (Ctr), without the hydrolysis treatment, the pan or total ubiquitin antibody labels all ubiquitinated proteins on immunoblots because the pan or total ubiquitin antibody recognizes the ubiquitin portion or non-ubiquitination sites of ubiquitinated proteins that are not the hidden common ACE epitope and thus they are already present without hydrolysis treatment. In comparison, as shown in immunoblot (ii) lane 2 (Try=trypsin), with the hydrolysis (trypsin) treatment, the pan or total ubiquitin antibody labeling is dramatically reduced because the ubiquitin portion epitope recognized by the pan or total ubiquitin monoclonal antibody is not a hydrolysis resistant ACE epitope and thus damaged by trypsin treatment. Molecular weight standards are indicated on the left.

FIG. 7. Western blotting of the common sumoylated site ACE structure of all sumoylated proteins in a sample. The samples were subjected to immunoblot analysis. The immunoblot membranes were treated with a non-enzyme solution (lane 1=Ctr), or a GluC solution (lane 2=GluC) to create the common ACE structures of sumoylated proteins. Without the GluC treatment, the common ACE structures were not artificially created and thus not labeled with the common ACE antibody as shown in lane 1 (Ctr). With GluC treatment, the common ACE structures of sumoylated proteins were artificially created or exposed, and thus labeled with the common ACE antibody, as shown multiple sumoylated protein bands on the immunoblot membranes. Molecular weight standards are indicated on the left.

DETAILED DESCRIPTION

The invention summarized above may be better understood by referring to the following description, which should be read in conjunction with the accompanying claims and drawings in which like reference numbers are used for like parts. This description in which some examples of the embodiments of the inventions are shown, is to enable one to build and use an implementation of the invention, and is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent methods, designs, constructs, antibodies, kits, samples, and cell lines do not depart from the spirit and scope of the invention in its broadest form.

DEFINITIONS

As used herein, the terms "detection" "detecting", or "isolating" are interchangeable with discovering, uncovering, finding, recognizing, revealing, determining, examining, measuring, and the like.

As used herein the common conjugation site-specific epitope refers to those of the same portion or consensus sequence within a group of different ACE structures or the consensus sequence shared by a group of different ACE structures.

As used herein the common ACE antibody refers to those that specifically bind the common conjugation site-specific epitopes.

As used herein, "in situ" refers to a phenomenon or event occurred in exactly the original location, both in vivo and in vitro, including but not limited to, in whole or part of biological bodies or organisms, in isolated organs, cells, and organelles, in tissues or tissue sections (with or without fixation), in isolated or cultured cells, in body fluids or cell culture media, as well as on Western blot membranes, and any supporting matrices or surfaces, in chromatographic and centrifuge fractions, in reaction mixtures, and the like.

As used herein, "ex situ" is the opposite of "in situ", and refers to a phenomenon or event that does not occur in the original place both in vivo and in vitro.

As used herein, the term "hidden antigen" is often interchangeable with "hidden hapten or segment" or "ACE structure", and refers to an antigen epitope/segment/structure that, in its intact or natural form, is less antigenic and/or poorly accessible to large molecules including, but not limited to, antibodies. For example, an ACE structure may be a macromolecule-to-macromolecule conjugation site, or a segment normally located inside its parent macromolecule, or may be covered by other surrounding molecules/structure(s)/cell membranes either in situ or ex situ, and thus is poorly or not accessible to antibodies.

As used herein, the term "macromolecule" refers to a polymeric molecule with more than 2 same or different units, either in a linear or branched sequence, including, but not limited to, polypeptides, polysaccharides, lipids or phospholipids, and nucleic acids, poly(ADP-ribose), or any combinations of the above.

As used herein, the term "macromolecule-to-macromolecule conjugation" refers to that process in which one macromolecule conjugates to another same or different macromolecule via a covalent linkage.

As used herein, the term "carbohydrate" is interchangeable with the term "saccharide", typically referring to either polymeric or monomeric sugar molecules.

As used herein, the term "conjugation site" refers to the site where a covalent linkage is formed between two macromolecules, mostly terminal-to-sidechain branched conjugations, and occasionally molecular head-to-tail linear conjugations.

As used herein, the term "conjugation site-specific hapten" refers to a segment that contains a macromolecular conjugation site, which may need to be linked to an immunogenic carrier in order to become a complete antigen.

As used herein, the term "conjugation site-specific antibody" refers to antibody that can specifically recognize a macromolecular-to-macromolecular conjugation site derived from both macromolecular moieties.

As used herein, the term "sidechain" refers to a chemical group that is attached to or branches from a core part of the molecule called the "mainchain" or backbone. In polymers, side chains extend from a backbone structure.

As used herein, the term "hydrolytic enzyme" refers to proteases, glycosidases, lipases or phospholipases, nucleases, and the like, which are currently known or will be identified in the future and are capable of cleaving particular chemical bonds in macromolecules in a site-specific manner.

As used herein, the term "agent", may be interchangeable with "hydrolytic agent" or "chemical agent", and refers to chemicals or any other non-biological materials that are currently known or will be identified in the future, and are capable of cleaving particular chemical bonds in macromolecular backbones in a site-specific manner. Hydrolytic agents may include, but are not limited to, 2-nitro-5-thiocyanobenzoic acid (NTCB)+Ni that cleaves the peptide bond at cysteine loci (Degani and Patchornik, 1974); cyanogen bromide (CNBr) that cleaves at methionine loci; BNPS-skatole [2-(2-nitrophenylsulfenyl)-3-methylindole] that cleaves at tryptophan loci; and formic acid that cleaves at aspartate loci in protein backbones.

Hydrolytic proteases and agents include, but are not limited to, Arg-C proteinase, Asp-N endopeptidase, Asp-N endopeptidase+N-terminal Glu, BNPS-Skatole, caspase1, caspase2, caspase3, caspase4, caspase5, caspase6, caspase7, caspase8, caspase9, caspase10, chymotrypsin, clostripain (clostridiopeptidase B), CNBr, enterokinase, factor Xa, formic acid, glutamyl endopeptidase, granzymeB, hydroxylamine, iodosobenzoic acid, LysC, LysN, NTCB (2-nitro-5-thiocyanobenzoic acid), pepsin, proline-endopeptidase, proteinase K, staphylococcal peptidase I, tobacco etch virus protease, thermolysin, thrombin, trypsin, and the like.

The chemical bond-cleaving site specificities of hydrolytic enzymes or agents can be found in publicly accessible databases including, but not limited, to Swiss-Prot ExPASy and the National Center for Biotechnology Information.

Glycosylases include: glycosidases that hydrolyze O- and S-glycosyl compounds and enzymes that hydrolyze N-glycosyl compounds.

Glycosidases include, but are not limited to, exoglycosidase, endoglycosidases, any combination of exoglycosidase and endoglycosidases, and/or sialidase, fucosidase, mannosidase, galactosidase, xylosidase, and the like.

Lipases include, but are not limited to, triglyceride lipase, pancreatic lipase, lysosomal lipase, hepatic lipase, hormone-sensitive lipase, endothelial lipase, lingual lipase, and the like.

Phospholipases include, but are not limited to, phospholipase A1, phospholipase A2, phospholipase B, phospholipase C, phospholipase D, GPI-phospholipase C, GPI-phospholipase D, and the like.

Macromolecular conjugation enzymes include but are not limited to E3 ubiquitin-protein ligase; UBL ligase, carbohydrate transferase, poly (ADP-ribose) polymerase, fatty acyl transferase; autophagy-related protein ligase [e.g., autophagy-related gene (ATG) 3 and ATG10], sumoylation ligase, neddylation ligase, transglutaminase, and the like.

Macromolecular de-conjugation enzymes may include, but are not limited to, deubiquitination enzymes (DUBs) and UBL proteases; desumoylation enzymes or SUMO proteases; deglycosylation enzymes, lipases, phospholipases, poly (ADP-ribose) glycohydrolases (PARG), ADP-Ribosyl Protein Lyase (PARL), and the like.

Enzymes used in the invention may be natural, recombinant or chemically synthesized. They may be substantially pure, partially purified, or present in a crude biological sample.

As used herein, the term "organism" refers to all cellular life-forms including, but not limited to, prokaryotes and eukaryotes, non-cellular life-forms, and nucleic acid-containing entities including, but not limited to, bacteriophages and viruses.

As used herein, the term "sample or sample preparation" refers to a collection of inorganic, organic or biochemical molecules either in a pure or mixture form, either in nature (e.g., in a biological- or other specimen) or artificial type, either in heterogeneous or homogeneous form, either in isolated, partially isolated or non-isolated form, or either in solution or in a form immobilized or semi-immobilized on any supporting materials including but not limited to electrophoresis matrix (e.g., gel or capillary), Western blot membrane (e.g., nitrocellulose membranes), agarose support (e.g., gel or bead), nano particles, any supporting surface, cell culture plates, multiplex beads, or chromatographic supporting matrix, sucrose gradient medium. "Sample" further refers to a biological sample.

As used herein, the term "organism" refers to all cellular life-forms, including but not limited to prokaryotes and eukaryotes, as well as non-cellular life-forms, nucleic acid-containing entities, including but not limited to bacteriophage and viruses.

As used herein, the terms "biological sample" refer to a collection of a whole organism or a subset of its tissues, cells or component parts (e.g. body fluids, including but not limited to blood, serum, plasma, mucus, lymphatic fluid, synovial fluid, tears, cerebrospinal fluid, saliva, amniotic fluid, amniotic cord blood, urine, feces, vaginal fluid, and semen). "Biological sample" further refers to a homogenate, lysate, subcellular fraction or extract prepared from a whole organism or a subset of its tissues, cells or component parts, or a portion thereof. "Biological sample" also refers to sample preparations including but not limited to on electrophoretic and chromatographic gels, on Western, Southern, and Northern blot membranes, in isolated organelles, and in separated fractions.

As used herein, the term "tissue section" refers to a thin slice prepared from a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen).

As used herein, the term "conjugation site-specific antibody" further refers to one or more antibodies that may be natural or partially or wholly produced artificially, e.g. recombinant, or antibody fragments. A conjugation site-specific antibody may be polyclonal antibody, monoclonal antibody, bi- or multi-specific antibody, recombinant antibody, single-domain antibody, heavy-chain (VHH fragment) antibody, antibody fragment, humanized antibody, binding partner, heteroconjugate antibodies, antibody-like fusion protein, or antibody-like molecule. A conjugation site-specific antibody may be made in all immunoreactive animals or organisms including but not limited to rabbit, rat, mouse, sheep, horse and donkey, or in some cases, be a member of one, or a combination immunoglobulin classes, including: IgG, IgM, IgA, IgD, and IgE, $V_HH$ as well as antibody-like molecules.

As used herein, the term "de-conjugation site-specific antibody" refers to one or more antibodies that recognize the conjugation site in the non-conjugated form.

As used herein, the term "pan or total antibody" refers to one or more antibodies that recognize epitopes that are not located on the conjugation site.

The conjugation site-specific haptens or antigens may be used to select its binding partners by, for example, phage display or yeast display. The haptens or antigens include, but are not limited to, any chemical monomers or polymers, amino acids or peptides, carbohydrates, lipids or phospholipids, nucleotides, poly (ADP-riboses), and the like.

As used herein, the term "antigenicity" refers to the antigen capacity to stimulate the production of antibodies and the capacity to react with antibodies.

As used herein, the term "primary antibody" refers to antibody raised against an epitope of interest. The epitope can be a protein, peptide, carbohydrate, lipid, phospholipid, nucleic acid, any combination of the above, or any other macromolecules.

As used herein, the term "secondary antibody" refers to an antibody that binds to primary antibodies or antibody fragments. They are typically labeled with measurable probes for detection, purification, or cell sorting applications.

As used herein, the term "antibody-based method" refers any method with the use of antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, flow cytometry, affinity chromatography, and the like.

As used herein a multiplex assay is a type of assay that simultaneously measures multiple analytes in a single run/cycle of the assay.

As used herein, the term "immunoassay" refers to any antibody-based measurement of the content of any substance in a sample. The presence of antigen and/or antibody can be assayed. The most common method is to label either antigen or antibody with any suitably detectable materials including, but not limited to, enzymes, radioisotopes, magnetic or fluorescent labels, or nanoparticles.

As used herein, the term "Western blot" or its interchangeable term "immunoblot" refers to an analytical method for detection of proteins or modified proteins in a sample. It uses gel electrophoresis to separate molecules in a sample. The separated molecules are then transferred to a membrane (typically nitrocellulose) that can hold the macromolecules, where such macromolecules of interest can be detected specifically with antibodies.

As used herein, the term "Enzyme-Linked ImmunoSorbent Assay" or "ELISA" refers to any method of detecting the presence and level of an antibody or an antigen in a sample. There are several variants of ELISA, including, but not limited to, sandwich ELISA, competitive ELISA, indirect ELISA, ELISA Reverse and the like. The most common procedure is to coat an antibody or antigen onto a surface, and then to add molecules of interest (antigen or antibody) to the precoated surface so that an antibody to antigen complex can form. The tagged antibodies or antigens, or the added secondary antibody with a detectable tag, can then be detected with a readout system.

As used herein, the term "immunohistochemistry" commonly refers to a method of antibody-based localization of antigens in a sample, commonly in a tissue section. An antibody to antigen interaction can be visualized by microscopy at the cellular level via any detectable means including, but not limited to, antibodies tagged by fluorophors, chromospheres or luminescence, or any detectable tags with any combinations of the above, including, but not limited to, peroxidase and its variants, chemiluminescence and its variants, and fluorescent molecules such as fluorescein isothiocyanate (FITC), Texas Red, rhodamine (TRITC), coumarin, cyanine, Alexa Fluors and the DyLight Fluors, and their derivatives.

As used herein, the term "immunocytochemistry" is often interchangeable with immunohistochemistry. Immunocytochemistry emphasizes a method of using antibodies to detect specific antigens at the cellular level. Immunocytochemistry may differ somewhat from immunohistochemistry in that it is often performed on samples of intact cells, whereas immunohistochemical samples are usually on tissue sections.

As used herein, the term "immunoprecipitation" refers to a technique of antibody precipitating its antigen molecule out of mixture samples. This process is often used to isolate and concentrate a particular antigen or antigen complex from other molecules in a sample. Immunoprecipitation often requires coupling antibody-antigen complexes to a solid support substance in the procedure for separation of antibody-antigen complexes from other molecules in a sample.

As used herein, the term "co-immunoprecipitation" refers to immunoprecipitation of intact antigen complexes.

As used herein, the term "flow cytometry" refers to a method of counting, examining, and sorting particles suspended in a stream of fluid. It allows simultaneous multi-parametric analysis of the physical and/or chemical characteristics of single cellular particles flowing through an optical and/or electronic detection apparatus.

"Post-translational modification" refers to any chemical modification of a polypeptide chain during and after it is synthesized, including but not limited to phosphorylation, acylation, acetylation, methylation, sulfonation, glycosylation, lipidation, prenylation, isoprenylation, ubiquitination, biotinylation, formylation, citrullination, myristoylation, sumoylation, gamma carboxylation, ADP-ribosylation, amidation, covalent attachment of a moiety including but not limited to flavin, heme, nucleotide or nucleotide derivative, phosphotidylinositol, cyclization, demethylation, formation of covalent cross-links including but not limited to transglutaminase-mediated protein cross-linking, formation of pyroglutamate, GPI anchor formation, hydroxylation, iodination, oxidation, proteolysis processing, racemization, selenoylation, and the like. A post-translational modification may also involve cleavage of the polypeptide chain, proteolytic processing, the formation of disulfide bonds, and the like.

As used herein, the term "glycosylation" refers to the enzymatic or non-enzymatic process that links at least one saccharide moiety to proteins, lipids or other macromolecules. The majority of proteins synthesized in the rough endoplasmic reticulum (ER) undergo glycosylation. Glycosylation also occurs in the cytoplasm and nucleus including, but not limited to, the O-GlcNAc (N-acetylglucosamine) modification. Cells can produce several classes of glycans including, but not limited to: N-linked glycan attached to the amide nitrogen of asparagine sidechain of a polypeptide; O-linked glycan attached to the hydroxyl oxygen of serine and threonine sidechain of a polypeptide; glycosaminoglycans attached to the hydroxyl oxygen of serine in a polypeptide; glycolipids in which glycans are attached to ceramide and hyaluronan, and GPI anchors which link proteins to lipids via glycan linkages.

"Core fucosylation" refers to the linkage of a fucose residue to the core N-acetylglucosamine via alpha1-6 linkage. All N-linked glycan structures have a common structure, referred to as the core, containing three mannose and two N-acetylglucosamine residues.

As used herein, the term "glycoform" refers to a group of proteins having an identical backbone amino acid sequence but different carbohydrate moieties.

As used herein, "artificially cleaved epitope or ACE" refers to an epitope that is artificially cleaved for creating more antigenic and accessible epitope to antibody for detection or forming antibody-to-ACE complex purpose.

The "Artificially Cleaved Epitope" or "ACE" does not include naturally cleaved antigens in vivo.

As used herein, "hydrolysis-guided ACE design or ACE design" refers to antigen design methods that use an artificially cleaved epitope (ACE) as a hapten or antigen. The ACE is not naturally accessible to antibody or antibody-like molecules but can be artificially, specifically and precisely created and/or exposed in a sample by the chemical bond-specific hydrolysis of macromolecules.

As used herein, "hydrolysis-guided ACE antibody production" is interchangeable with "ACE antibody production" refers to making antibody with an ACE hapten or antigen designed by the ACE design methods.

As used herein, "residue" and "monomer" (of macromolecules) is often interchangeable, refers to a specific unit within polymeric chains of peptides, polysaccharides, lipids, nucleic acids, poly(ADP-ribose), and the like.

As used herein, "create or expose" (of ACE antigen) is often interchangeable.

As used herein, the term "create" refers to artificially creating ACE structures with free terminals in samples or sample preparations for antibody detection.

As used herein, "ACE methods" refers to a group of collective techniques including, but not limited to: (i) ACE design, (ii) making ACE antibody, (iii) ACE exposure and detection either in situ or ex situ in a sample, and (iv) ACE method applications.

Methods of Design Ace Antigens

Extensive efforts on generation of the common macromolecule-to-macromolecule conjugation site-specific antibodies by conventional antibody methods for antibody-based applications have been proven futile (Matsumoto et al., 2008). A key reason is that most macromolecule-to-macromolecule conjugation sites are either poor antigen or hidden inside of the conjugated macromolecules, and thus poorly or not accessible to antibody binding. This invention provides novel methods to solve these problems. These methods are generally and collectively referred to as the "hydrolysis-guided ACE methods" or simply "ACE methods", including, but not limited to, all or part of these steps: (i) preparing, generating or isolating a common ACE structure; (ii) the common ACE structure is a non-cleaved segment of an intact macromolecule in vivo, and is either poorly antigenic, or not accessible by antibody, but can be artificially and specifically created and/or exposed by a residue chemical bond-specific hydrolytic enzyme or agent, or by their combinations, (iii) conjugate the ACE hapten to an immunogenic carrier for making it a complete antigen, (iv) a spacer may sometimes be added to increase the flexibility of the ACE, (v) use the complete antigen to make the antibodies, antibody-like molecules, or binding partners, (vi) purify the common ACE-specific antibody, (vii) create and/or expose the ACE artificially, specifically and precisely, rather than randomly or accidentally, either in situ or ex situ in any sample preparations by the specifically designated chemical bond-specific hydrolytic enzyme or means, and (viii) detect, isolate, or image the common ACE structure in a sample or a sample preparation by antibody-based methods.

The Common Macromolecular Conjugation Site-Specific ACE Structure Design.

The ACE methods for designing a common ACE structure are based on information of: (a) the molecular structure and ACE sequence, (b) availability and property of chemical bond-specific hydrolytic enzymes or agents, and (c) methods of sample analyses. Therefore, the ACE methods are highly predictable, reliable and sensitive. Generally, the ACE structure at a hidden macromolecule-to-macromolecule conjugation site has all or part of these characters: (i) comprises of a shorter piece (usually 1-50 monomers) derived from one macromolecule and a longer piece (usually 1-100 monomers) derived from another macromolecule; (ii) must be antigenic; and (iii) is poorly exposed and/or poorly antigenic naturally or in vivo, and thus needs to be artificially, specifically and precisely created (free terminals) and/or exposed in a sample and a sample preparation by chemically engineered means, including, but not limited to, by using chemical bond-specific hydrolytic enzymes, agents, or their combinations.

A macromolecule-to-macromolecule conjugation site-specific ACE structure can be described as: Ln------L2-L1(-S1-S2------Sm)-L1'-L2'------Lm', or Ln------L2-L1-L1'-L2'------Lm(-S1-S2------Sm)' wherein L(# or #')s stand for residues and their numbers of one (e.g., long) macromolecular segment which has either a branched or a linear covalent conjugation with a second macromolecule at L1 or Lm'; wherein S(#)s stand for residues and their numbers of the second (e.g., short) macromolecular segment in which S1 is covalently conjugated to either L1 or Lm'; wherein L1, L2 etc. are counted toward one direction; wherein L1', L2' etc. are counted toward the opposite direction; wherein S1, S2 etc. are counted toward the third or branched direction from the conjugation site; wherein the conjugation site is located between L1 and S1 or between Lm' and S1; wherein n, m and m' are residue numbers continuously counted from the L1, L1' and S1, respectively; wherein Ln, Lm', or Sm are not free ends naturally and have natural chemical bonds with residues outside of the ACE structure; and wherein the nature chemical bonds between Ln, Lm' or Sm and the outside residues can be artificially, specifically and precisely cleaved by a chemical bond-specific hydrolysis in any sample preparations to create and expose the ACE structure(s) for detection. Examples of the common ACE structures are shown in FIGS. 1-4. By using the inventive ACE methods, we have successfully made several common ACE antibodies that are highly specific to the common ACE structures as shown in FIGS. 5-7.

The ACE methods can also be used to reduce antibody non-specific bindings in all antibody-based methods. The reduction of antibody non-specific binding is owing to the fact that the ACE methods can artificially, precisely and specifically create and/or expose the ACE, while breaking up the antibody non-specific binding structures.

Examples of the Common SUMO Conjugation Site-Specific ACE Antigen Designs (No SEQ ID NOs are assigned to sequences of this example because they are branched peptides)

SUMO can conjugate to many proteins including itself by an isopeptide bond. There are at least 4 SUMO isoforms in humans; SUMO-1, SUMO-2, SUMO-3 and SUMO-4, all of which contains the C-terminal G-G that conjugated to a lysine (K) of a protein. As demonstrated in FIG. 1A, based on the consensus sequence hΨ-K-X-D/E, a common sumoylation site-specific ACE epitope is designed as C-X---hΨ-K(-G-G-X---E/D)-X-E/D, wherein the shade area represents the common ACE epitope, wherein C is a cysteine residue for conjugation to an immunogenic carrier such as KLH, wherein (hΨ) is any amino acid, but preferably a non-nature hydrophobic D- or homo-amino acid such as beta-(homo)alanine, beta-(homo)valine, beta-(homo)lucine, beta-(homo)isolucine, or beta-(homo)phenylalanine, wherein X is any amino acid but preferably a non-nature hydrophilic D- or homo-amino acid such as beta-homoproline, beta-homoserine, beta-homothreonine, or beta-homoasparagine, wherein X--- represent 0-50 different X residues; wherein different X--- residues are arranged in a random or scrambled order, wherein (-G-G-X---E/D) is the branched peptide derived from the SUMO molecule. The antibody can be made with the common ACE structure conjugated to KLH, wherein the antibody binds the common ACE structure [-K(-G-G-)-] or the common ACE structure with the consensus sequence or motif [-K(-G-G-)-X-D/E] but antibody binding is independent of the X amino acid residues. After treatment either with endoproteinase GluC (Staphylococcus aureus Protease V8) for the glutamic acid (E), and/or endoproteinase AspN (flavastacin) for the aspartic acid (D) to artificially and specifically create and/or expose the common ACE structure either in situ or ex situ in a sample or a sample preparation, the common ACE conjugation site-specific epitopes can be detected or isolated with the ACE antibody by all antibody-based methods.

FIG. 1B shows alternative designs of the common sumoylation site-specific ACE epitopes C-X---hΨ-K-X-E (SEQ ID NO 1) C-X---hΨ-K-X-D (SEQ ID NO 1). This epitope is the same as in FIG. 1A but without the branched sequence (-G-G-X---E/D). After GluC or AspN treatment to create and/or expose the ACE structure either in situ or ex situ in a sample or a sample preparation, both X---hΨ-K-X-E/D and X---hΨ-K(-G-G-X---E/D)-X-E/D peptides will be created in the sample. The antibody can be made with the common ACE structure KLH-C-X---hΨ-K-X-E/D. The antibody can be used to remove the non-sumoylated peptide X---hΨ-K-X-E/D from the sample. The sample will be further treated with a desumoylation enzyme (e.g., SENT), which converts X---hΨ-P-K(-G-G-X---E/D)-X-E/D to X---hΨ-K-X-E/D. Therefore, the newly converted peptides with the X---hΨ-K-X-E/D structure in the sample can then be isolated with the antibody.

FIG. 1C illustrates another common sumoylation site-specific ACE epitope C-X---hΨ-K(-G-G-X---E/D-X---K/R)-X-E/D-X---K/R, wherein the shade area represents the common ACE epitope, wherein C, hΨ, X, and X--- residues(s) are same as in FIG. 1A, wherein K/R are lysine (K) or arginine (R) residues. The common ACE antibody can be made with KLH-C-X---hΨ-K(-G-G-X---E/D-X---)-X-E/D-X---, wherein the antibody binds the common ACE structure -hΨ-K(-G-G-)- with the consensus sequence or motif -hΨ-K(-G-G-)-X-D/E but antibody binding is independent of X or K/R amino acid residues. After treatment with trypsin to create and/or expose the ACE structure either in situ or ex situ in a sample or a sample preparation, the common ACE epitopes can be detected or isolated with the ACE antibody by all antibody-based methods.

FIG. 1D displays additional designs of the common sumoylation site-specific ACE epitopes C-X---hΨ-K-X-E/D-X---K (SEQ ID NO 1) and C-X---hΨ-K-X-E/D-X---R (SEQ ID NO 1) that is the same as in FIG. 1C but without the branched sequence (-G-G-X---E/D-X---K/R). The common ACE antibody (that recognizes -hΨ-K-X-E/D but is independent of X residues) can be made with KLH-C-X---hΨ-K-X-E/D-X--- antigen immunization. Trypsin treatment of a sample can create both X---hΨ-K-X-E/D-X---K/R and X---hΨ-K(-G-G-X---E/D-X---K/R)-X-E/D-X---K/R peptides in the sample. The antibody can be used first to remove the non-sumoylated peptides with the X---hΨ-K-X-E/DX---K/R structure from the sample. The sample can be further treated with a desumoylation enzyme (SENT), which converts X---hΨ-K(-G-G-X---E/D-X---K/R)-X-E/D-X---K/R to X---hΨ-K-X-E/D-X---K/R. Therefore, the newly converted peptides with the common -hΨ-K-X-E/D- structure can then be detected or isolated from the sample with the antibody by any antibody-based methods.

FIG. 7 shows a Western blot application of the common sumoylated site ACE antibody to detect the common ACE structures in a sample. The samples were subjected to immunoblot analysis. The immunoblot membranes were blocked with BSA and treated with a non-enzyme solution (lane 1=Ctr), or a GluC solution (lane 2=GluC) to create the common ACE structures of sumoylated proteins on the immunoblot membranes. Without the GluC treatment, the common ACE structures were not artificially created and thus were not labeled with the common ACE antibody as shown in lane 1 (Ctr). With GluC treatment, the common ACE structure of sumoylated proteins was artificially created, and thus was labeled with the common ACE antibody, as shown multiple protein bands on the immunoblot membranes.

Examples of the Common Glycosylation Site-Specific ACE Antigen Design

Many proteins such as alpha-fetoprotein (AFP), transferrin, and alpha-1-antitrypsin (A1AT) are glycosylated at the asparagine (N) residue by polysaccharides via the N-link bond. Addition of a fucose to the innermost (also referred to as "core") N-acetylglucosamine (-GlcNAc) of the glycan via the alpha(1,6) bond (i.e., core-fucosylated or -GlcNAc-Fuc) of N-linked glycosylated proteins are related to cancers, such as hepato-cellular carcinoma (HCC), pancreatic, prostate, colon, lung, and gastrointestinal cancers (Otake et al., 2001; Kossowska et al., 2005; Hu et al., 2008; Miyoshi et al., 2010; Osumi et al., 2009; Narisada et al., 2010; Moriwaki et al., 2010; Saldova et al., 2010; Wu et al., 2010). For that reason, the common glycosylation site-specific antibodies are useful not only for identifying, detecting or isolating glycosylated proteins or peptides, but also valuable for R&D, diagnostic and therapeutic applications of different types of cancers and diseases. However, this type of antibodies cannot be made with general antigens owing to steric hindrance from the long and folded polysaccharide chain and its conjugated protein. The present invention provides methods and antibodies for detecting and isolating the common ACE structure for MS application and any other antibody-based applications.

N-linked protein glycosylation site has a consensus sequence N-X-S/T. The ACE methods can be used to design the common glycosylation site-specific ACE antigens. The common N-link glycosylation site-specific ACE epitopes can be designed as C-X---N(-GlcNAc)-X-S- (SEQ ID NO 2) and C-X---N(-GlcNAc)-X-T- (SEQ ID NO 2) (FIG. 2A), and C-X---N(-GlcNAc-Fuc)-X-S- (SEQ ID NO 2) and C-X---N(-GlcNAc-Fuc)-X-T- (SEQ ID NO 2) (FIG. 2B), respectively, wherein the shade areas represent the common ACE structures, wherein C is a cysteine residue for conjugation of the hapten to an immunogenic carrier such as KLH, wherein S/T denotes either serine (S) or threonine (T) residue, wherein X is any amino acid but preferably a non-nature hydrophilic D- or homo-amino acid such as beta-homoproline, beta-homoserine, beta-homothreonine, or beta-homoasparagine, wherein X---represent 0-50 different X residues; wherein different X residues are arranged in a random or scrambled order, wherein GlcNAc is N-acetyl-D-glucosamine, wherein GlcNAc-Fuc is a fucosylated GlcNAc (disaccharide) either via an alpha 1,6 linkage or any other linkage, wherein GlcNAc or GlcNAc-Fuc is covalently conjugated to an asparagine (N) residue via either a N-link bond or any other linkage. The common ACE antibodies can be made with KLH-C-X---N(-GlcNAc)-X-S/T, and C-X---N(-GlcNAc-Fuc)-X-S/T, respectively, wherein antibody binding to the common ACE structure -N(-GlcNAc)- or -N(-GlcNAc-Fuc)-, or binding to the common ACE structure with the consensus sequence -N(-GlcNAc)-X-S/T- or -N(-GlcNAc-Fuc)-X-S/T-, wherein the antibody binding is independent of X residues. After treatment with a endoglycosidase (D, F, F1, F2 or H) or combinations of endoglycosidases, endoglycosidases in combinations with protease to create and/or expose the ACE structure either in situ or ex situ in a sample or a sample preparation, the common ACE conjugation site-specific epitope can be detected or isolated with the corresponding ACE antibody by all antibody-based methods.

FIG. 2C shows another common glycosylation site-specific ACE epitopes C-X---N-X-S-X--- (SEQ ID NO 2) and C-X---N-X-T-X--- (SEQ ID NO 2), wherein C, X---, X, S, and T are the same as in FIG. 2A. The antibody can be made with KLH-C-X---N-X-S/T-X---, wherein antibody binds to the consensus -N-X-S/T- motif, and wherein antibody binding is independent of X residues or the GlcNAc residues. Protease (e.g., trypsin) or protease plus endoglycosidase treatment of a sample can create both X---N(-GlcNAc-X---)-X-S/T-X---K/R (SEQ ID NO 2) and X---N-X-S/T-X---K/R (SEQ ID NO 2) in the sample, wherein X---N-S/T-X---K/R peptides can be removed first with the antibody while X---N(-GlcNAc-X---)-X-S/T-X---K/R structure remains in the sample, wherein saccharide residue(s) (-GlcNAc-X---), (-GlcNAc), or (-GlcNAc-Fuc) can be removed from X---N(-GlcNAc-X---)-X-S/T-X---K/R, X---N(-GlcNAc)-X-S/T-X---K/R or X---N(-GlcNAc-Fuc)-X-S/T-X---K/R structures in the sample with N-glycosidase F (also known as PNGase F) or combinations of PNGase with endoglycosidases to create a new X---N-X-S/T-X---K/R structure. Therefore, the newly created common ACE structures with the common X---N-X-S/T-X---K/R can then be detected or isolated with the antibody by any antibody-based method.

We used the common ACE structure C-X---N(-GlcNAc)-X-S/T- to make a common glycosylation site-specific antibody. FIG. 5 demonstrates the Western blot application of this common glycoform-specific antibody. Samples from the cell culture media were treated with a non-enzyme solution (Ctr) (so that all polysaccharide moieties remain on the proteins or peptides), a mixture of endoglycosidases-D and -H (endo-D/H) to create mono-saccharide-proteins or -peptides, or a general PNGase-F (F) solution to remove all mono- or polysaccharide moieties from proteins or peptides. Samples were then subjected to immunoblot analysis.

Immunoblots were labeled with: (i) the common ACE antibody that recognizes the common ACE structure [-N(-GlcNAc)-] of glycosylated proteins, (ii) a pan or total anti-transferrin antibody (that binds the non-glycosylated segment of the protein and thus recognizes both glyco- or non-glyco-form of transferrin), (iii) a pan or total anti-AFP antibody that binds the non-glycosylated segment of the protein, and (iv) a pan or total anti-alpha-1-antitrypsin (A1AT) antibody that binds the non-glycosylated segment of the protein. As shown in immunoblot (i), the common ACE antibody binds only the mono-glyco-form after endo-D/H treatment of glycosylated proteins in the sample but does not recognize the poly-glyco-form (Ctr=non-enzyme solution treatment) or de-glyco-form [PNGase-F (F) treatment] of glycol-proteins. In comparison, the pan or total antibodies detect all three forms of the proteins in the samples, respectively as shown in immunoblots (ii), (iii) and (iv). This is because these pan or total antibodies bind the non-glycosylation segments of the proteins and thus they are independent of deglycosylation treatments.

Examples of the Common Ubiquitin-to-Protein Conjugation Site-Specific Hidden ACE Antigen Design.

A common ubiquitin site-specific ACE epitope is designed as C-X---K(-G-G)-X---K/R (No SEQ ID NO is assigned to this sequence because it is a branched peptide), wherein the -K(-G-G)- represents the common ACE epitope, wherein C is a cysteine residue for conjugation to an immunogenic carrier such as KLH, wherein X--- represent 0-50 different amino acids selected from both natural and nature aminoacids but preferably from non-natural hydrophilic D- or homo-amino acids such as beta-homoproline, beta-homoserine, beta-homothreonine, or beta-homoasparagine, wherein different X residues are arranged in a random or scrambled order, wherein (-G-G) is the branched dipeptide derived from the c-terminus of the ubiquitin. The antibody can be made with the common ACE structure conjugated to KLH, wherein the antibody binds the common ACE structure but antibody binding is independent of X amino acid residues. After treatment of a sample with trypsin and/or lysyl endopeptidase (LysC) to create the ACE structure either in situ or ex situ in a sample or a sample preparation, the common ACE conjugation site-specific epitopes can be detected or isolated with the ACE antibody by all antibody-based methods such as Western blot and immunohistochemistry.

We used the common ACE structure X---K(-G-G)-X--- to make a common ubiquitin-to-protein conjugation site-specific antibody. This antibody binds to the common ACE structure -K(-G-G)- but independent of X--- residues. FIG. 6 displays a Western blot application using the antibody against the common ACE structure. The cell lysate samples were subjected to immunoblot analysis. Immunoblot membranes (i) and (ii) were blocked with BSA and treated with a non-enzyme solution as a control (lane 1=Ctr), or a trypsin solution (lane 2=Try) to create the ACE structure in the immunoblot membranes. After washing and blocking of non-specific binding, the immunoblot membranes were labeled with: (i) the common ACE antibody, and (ii) a pan or total ubiquitin antibody (Chemicon MAB1510). This pan or total ubiquitin antibody (Chemicon MAB1510) recognizes the ubiquitin moiety of ubiquitinated proteins, and thus does not recognize the common ACE structure -K(-G-G)-. As shown in immunoblot (i) lane-1 (Ctr), without the hydrolysis treatment of the sample preparation, the common ACE antibody cannot detect the common ACE structure because they were not created by the hydrolysis treatment. In compassion, as shown in immunoblot (i) lane 2 (Try=trypsin), with the hydrolysis (trypsin) treatment of the sample preparation, the common ACE antibody can detect the common ACE structures of all ubiquitinated proteins because the common ACE structures from all ubiquitinated proteins were created by the hydrolysis treatment. On the contrary, as shown in immunoblot (ii) lane 1 (Ctr), without the hydrolysis treatment of the sample preparation, the pan or total ubiquitin antibody labels all ubiquitinated proteins on immunoblots because the pan or total ubiquitin antibody recognizes the ubiquitin portion that are not the hidden common ACE epitope and thus they are already exposed without hydrolysis treatment. In comparison, as shown in immunoblot (ii) lane 2 (Try=trypsin), with the hydrolysis (trypsin) treatment, the pan or total ubiquitin antibody labeling is dramatically reduced because the ubiquitin portion epitope recognized by the pan or total ubiquitin monoclonal antibody is not a hydrolysis resistant ACE structures and thus damaged by trypsin treatment.

Examples of the Common ADP-Ribosylated Protein Conjugation Site-Specific ACE Structure Design.

Adenosine diphosphate (ADP)-ribosylation is a reversible posttranslational modification of proteins wherein a single unit (mono-ADP-ribosylation) or a polymeric chain (poly-ADP-ribosylation) of ADP-ribose residue(s) is conjugated to a protein by mono-ADP-ribosyltransferases or poly-ADP-ribosyltransferases (PARPs). ADP-ribosylation is involved in many cellular processes, including, but not limited to, cell signaling, DNA repair, gene regulation, genomic stability, mRNA translation, protein degradation, inflammation, and cell death. Improper ADP-ribosylation has been implicated in diseases including, but not limited to, cancers, diabetes, neurodegenerative disorders, stroke, and heart failure. Some bacterial compounds such as cholera toxin, diphtheria toxin, pertussis toxin, heat-labile enterotoxin of *E. Coli*, exotoxin A, C3 toxin and many others, exert their toxicities via ADP-ribosylation of proteins such as GTP-binding proteins (e.g., Rho, Ras, Gi, Go, and Gt) and ribosomal elongation factor EF-2. Therefore, bacterial toxin ADP-ribosylated proteins can be used as biomarkers of bacterial infections of particular diseases. Because of the importance, many therapeutic PARP inhibitors have been developed. Therefore, development methods and antibodies for antibody-based detection or isolation of ADP ribosylated proteins can create significant value.

Mono-ADP-ribosylation is initiated by mono-ADP-ribosyltransferases which conjugate an ADP-ribose residue onto arginine, glutamic acid, or aspartic acid residues in substrate proteins. Poly(ADP-ribosyl)ation is carried out by poly ADP-ribose polymerase (PARP) via transferring a poly-ADP-ribosyl chain onto proteins. Poly(ADP-ribose) glycohydrolase (PARG) or ADP-ribosylhydrolase 3 (ARH3) cleaves the bond between the innermost ADP-ribosyl residue and the rest of poly-ADP-ribosyl chain, to produce mono-ADP-ribose-protein (Gagné et al., 2005).

Several attempts have been made to produce antibodies to ADP-ribosylated residues. However, most of ADP-ribosylated residue antibodies lack specificity. Furthermore, these antibodies bind the poly-ADP ribose chain but do not recognize mono-ADP ribosylated protein (Laing et al., 2011).

The enrichment of mono-ADP-ribosylated proteins or peptides is a critical determinant of successfully identifying ADP-ribosylated proteins in a sample by e.g., mass spectrometry (MS) analysis (Daniels et al., 2015). Currently, the mostly used is an immunoaffinity isolation of poly(ADP-ribose) polymers longer than 20 subunits with the 10H antibody. However, these 10H antibody-based enrichment methods are mainly for poly(ADP-ribose) polymers and cannot differentiate mono- from poly-ADP-ribosylated proteins. The poly(ADP-ribose) glycohydrolase (PARG) and ADP-ribosylhydrolase 3 (ARH3) have been used to efficiently convert a poly-ADP-ribosylated protein or peptide to a Mono-ADP-ribosylated protein or peptide. Because mono-ADP-ribosylated peptide has a 541.06 Dalton mass shift, isolation or enrichment of mono-ADP-ribosylated protein or peptide will have significant advantage over the 10H antibody-based enrichment of poly-(ADP-ribose) polymers (Daniels et al., 2015). However, the antibody that specifically binds the mono-ADP-ribosylated proteins or peptides is not currently available. The inventive ACE methods and antibodies can be used to isolate mono-ADP-ribosylated protein or peptide. Furthermore, The pyrophosphatases, e.g., snake venom phosphodiesterase (SVP) or NudT16) can effectively convert poly-ADP-ribosylated proteins or peptide to phospho-ribosylated (P-ribosyl) proteins or peptides. A hydrolytic agent hydroxylamine (HL) can be used to cleave the ADP-ribosyl moiety from acidic (glutamic and aspartic) amino acid residues. The resultant hydroxamic acid derivative (HAD) has a mass shift of 15.01 Daltons, which is easily distinguishable by MS for identifying acidic ADP-ribosylation sites (Zhang et al., 2013). The IMAC or TiO2 materials have been used to isolate ADP-ribosylated peptide, but the specificities are significantly lower than antibody-based methods (Laing et al., 2011). However, the methods and antibodies for specifically isolating these hydrolyzed moieties (Mono-ADP-ribos-, P-ribose-, and HAD-proteins or -peptides) are not currently available. This invention provides methods and antibodies for specifically isolating or detecting these common ACE moieties, and can also be used to separate mono- from poly-ADP-ribosylated proteins or peptides (see FIG. 3 below). Therefore, the inventive ACE method and antibody have distinctive and significant advantage relative to the methods described in the prior art.

As shown in FIG. 3, poly-ADP-ribose-protein or -peptide can be converted to: (i) mono-ADP-ribose-protein or -peptide with PARG/ARH3 or PARG/ARH3 plus a protease in a sample or a sample preparation (such as a Western blot membrane, cell culture, or tissue section); (ii) phosphoribose (P-ribose)-protein and -peptide via a phosphodiesterase or phosphodiesterase plus a protease in a sample or a sample preparation; and (iii) a hydroxamic acid derivative (HAD)-protein or -peptide by hydroxylamine (HL) or HL plus a protease in a sample or a sample preparation. Several amino acid sidechains can be conjugated with a ADP-ribosyl residue, including glutamic (E) and aspartic (D) acids, serine (S), threonine (T), phosphoserine (pS), asparagine (N), arginine (R), lysine (K), and diphthamide. In this invention, these ADP-ribosylated amino acids are collectively referred to as Ω residue(s). The ADP-ribosylated glutamic and aspartic acids are sensitive, whereas ADP-ribosylated lysine sites are insensitive to the HL treatment. Furthermore, the ADP-ribosylated arginine (R) residue has a highly conserved R-S-E-X-E motif. Therefore, the common ADP-ribosylation site-specific ACE epitopes can be designed as: (i) C-X---Ω(-ADP-ribose)-X--- (SEQ ID NO 3); (ii) C-X---Ω(-P-ribose)-X--- (SEQ ID NO 3); and (iii) C-X---E(-HAD)-X--- (SEQ ID NO 4) and C-X---D(-HAD)-X--- (SEQ ID NO 5), wherein the shade areas represent the common ACE epitopes, wherein C is a cysteine residue for conjugation to an immunogenic carrier such as KLH, wherein X--- represent 0-50 different residues of a polymer (e.g., amino acids or ADP-riboses), whereas different X amino acid residues are selected from both natural and nature aminoacids but preferably from non-nature hydrophilic D- or homo-amino acids such as beta-homoproline, beta-homoserine, beta-homothreonine, or beta-homoasparagine, wherein different X amino acid residues are arranged in a random or scrambled order, wherein (-ADP-ribose), (P-ribose) and (-HAD) are conjugated to the side chains of the Ω residue. The antibody can be made with the corresponding common ACE structure conjugated to KLH, wherein the antibody binds the common ACE structure but antibody binding is independent of X amino acid or poly-ADP-ribose residues. After treatment of a sample with (i) PARG or ARH3 with/without a protease; (ii) SVP or NudT16 (both are phosphodiesterases) with/without a protease; or (iii) hydroxylamine with/without a protease, to artificially create the ACE structure either in situ or ex situ in a sample or a sample preparation, the common ACE conjugation site-specific epitopes can be detected or isolated with the ACE antibody by all antibody-based methods.

Alternatively, the common ACE antibody to the mono-ADP-ribosylated lysine consensus R-S-E-X-E motif can also be made with the common ACE structure C-X---R(-ADP-ribose)-S-E-X-E-X--- (SEQ ID NO 6), C-X---R(-P-ribose)-S-E-X-E-X--- (SEQ ID NO 6), or C-X---R(-HCD)-S-E-X-E-X--- (SEQ ID NO 6). Additionally, the common ACE antibody can also be made with the consensus motif C-X---R-S-E-X-E-X--- (SEQ ID NO 6) without ADP-ribosyl moiety. In this case, the ADP-ribosylated protein or peptide can then be detected or isolated after de-ADP-ribosylation with an ADP-Ribosyl Protein Lyase (PARL). Furthermore, the ADP-ribosyl hydrolysis treatments can be either alone or in combinations with protease(s). The hydrolysis treatments can be carried out at the same time or sequentially. The protease is selected from any chemical bond specific hydrolytic enzymes or agents, or their combinations thereof.

Examples of the Common GPI-to-Protein Conjugation Site-Specific ACE Design.

GPI is post-translationally conjugated to a group of structurally and functionally diversified proteins via an ethanolamine linker. This group of proteins is anchored in the outer leaflet of the cell membrane. The GPI-anchor structure can be selectively and specifically cleaved by several hydrolytic enzymes and agents. As shown in FIG. 4, nitrous acid treatment of a GPI anchor-containing sample at room temperature (pH 4.0) can specifically and selectively cleave the glucosamine-inositol glycosidic bond to create a common ACE structure on the GPI glycan that has a free reducing terminus in the form of 2,5-anhydromannose (referred to as GPI-AM hereafter). This terminus can further be reduced to 2,5-anhydromannitol (AHM) by sodium borotritide (NaBH4) (referred to as GPI-AHM hereafter), thus providing an opportunity to introduce an isotopic hydrogen ion for MS detection. This terminus can also be attached with the different reactive compounds (Com) such as 2-aminobenzamide (referred to as GPI-Com hereafter) to form a fluorescence labeled terminus. Therefore, the common ACE structures with GPI-AM, GPI-AHM and GPI-Com conjugations can be used to generate the common ACE antibodies to these ACE structures. Furthermore, GPI anchor can be specifically cleaved with phospholipase C (PLC) or D (PLD). GPI anchor cleaved by PLC creates a structure known as cross-reacting determinant (CRD) (referred to as GPI-CRD hereafter). The CRD can be used to generate the specific antibody (Zamze et al., 1988). The present invention provides the ACE methods for making antibodies to detect these common ACE structures, as these ACE structures can be artificially created in a sample or a sample preparation and detected or isolated by any antibody-based methods such as Western blotting and immunohistochemistry.

As shown in FIG. 4, the common GPI anchor ACE structures are designed as: (i) C-X---X-GPI-AM (SEQ ID NO 7); (ii) C-X---X-GPI-AHM (SEQ ID NO 7); (iii) C-X---X-GPI-Com (SEQ ID NO 7); and (iv) C-X---X-GPI-CRD (SEQ ID NO 7), respectively, wherein the -X-GPI-AM, -X-GPI-AHM, -X-GPI-Com, and -X-GPI-CRD are the common ACE epitopes, wherein C is a cysteine residue for conjugation to an immunogenic carrier such as KLH, wherein X--- represent 0-100 different amino acid residues, whereas different X amino acid residues are selected from both natural and nature aminoacids but preferably from non-nature hydrophilic amino acids such as D-amino acids or homo-amino acids (e.g., beta-homoproline, beta-homoserine, beta-homothreonine, or beta-homoasparagine), and wherein different X amino acid residues are arranged in a random or scrambled order. The antibody can be made with the corresponding common ACE structure conjugated to an immunogenic carrier such as KLH, wherein the antibody binds the common ACE structure but antibody binding is independent of X residues. After treatment of a sample with (i) nitrous acid with/without a protease; (ii) nitrous acid and then NABH4 together with/without a protease; (iii) nitrous acid and then the compound with/without a protease, and (iv) phospholipase C (e.g., phosphoinositide phospholipase C=PI-PLC) with/without a protease to create and/or expose the ACE structure either in situ or ex situ in a sample or a sample preparation, the common ACE conjugation site-specific epitopes can be detected or isolated with the ACE antibody by all antibody-based methods.

The step of preparing an ACE structure may further comprise treating the ACE structure with cross-linkers or fixatives. This step is for making the ACE antibody that recognizes the ACE structure that is treated with the cross-linkers or fixatives in a sample or a sample preparation. The role of treatment of the ACE structure with cross-linkers or fixatives is to keep ACE antigens in the samples or sample preparations after hydrolysis so that the ACE structure will not be reduced or moved in the samples or sample preparations during analysis. Cross-linkers or fixatives can be selected from any cross-link, adhesion, covalent or noncovalent conjugating chemicals including, but not limited to: chemical crosslinking agents such as the imidoester cross-linker dimethyl suberimidate, the N-hydroxysuccinimide-ester crosslinker BS3 and formaldehyde, the zero-length carbodiimide crosslinker EDC, SMCC or its water-soluble analog, Sulfo-SMCC, and the like. Fixatives also include aldehyde such as formaldehyde, paraformaldehyde, and glutaraldehyde, alcohol, acetone, and osmium tetroxide, and the likes.

Methods of Making Ace Antibodies

The present invention further discloses methods of using ACE antigens to make ACE antibodies. Such antibodies can be made with ACE antigens in conjunction with all antibody making methods. Exemplary antibodies may be polyclonal antibody, monoclonal antibody, bi- or multi-specific antibody, recombinant antibody, single-domain antibody, heavy-chain ($V_H$H fragment) antibody, antibody fragment, humanized antibody, binding partner, or an antibody-like molecule.

Common ACE Polyclonal Antibodies:

The ACE polyclonal antibody can usually be made by injecting the common ACE antigens into animals including, but not limited to, chickens, goats, guinea pigs, hamsters, horses, mice, rats, sheep and the like. Specific ACE haptens are usually linked to an immunogenic carrier including, but not limited to, KLH, serum albumin, bovine thyroglobulin, soybean trypsin inhibitor, or the like. Adjuvants are normally used to improve or enhance an immune response to antigens. Blood serum from these animals contains polyclonal antibodies, also known as antiserum, that bind to the same ACE hapten or antigen. Antigens may be also injected into chickens for generation of polyclonal antibodies in egg yolks.

Common ACE Monoclonal Antibodies:

The common ACE monoclonal antibody is normally derived from a single cell line and obtained by fusing antibody-secreting lymphocytes with a cancer cell line. A mouse, hamster, rat, rabbit or other appropriate host animal can typically be immunized with a complete ACE antigen made by attaching an ACE hapten to an immunogenic carrier. Alternatively, the lymphocytes may be immunized in vitro. Spleen cells immunized with ACE antigens are then fused with myeloma cells using a fusing agent to make hybridomas. A mixture of hybridomas is then diluted and subcloned. The clones from single parent cells are then selected. The antibodies produced from the single clones (monoclonal) are then tested for their binding affinity and specificity to the antigens by any single or combinations of antibody-based methods including, but not limited to, immunoblotting, immunohistochemistry, immunocytochemistry, immunoprecipitation, flow cytometry, peptide array, ELISA or all other immunoassays, or immunoelectron microscopy. The clones with the highest binding affinity and specificity to the ACE structures or clones for specific applications are then selected and grown in cultures or in the peritoneal cavity of animals to a high volume for the production of monoclonal antibodies.

Polyclonal and monoclonal antibodies can be purified using the common ACE hapten-conjugated matrices or resins, or by using Protein A/G or complete antigen-affinity chromatography for separation of antibodies from other molecules in crude antibody preparations. Negative absorptions may be required for separating conjugation site-specific antibodies from the non-conjugation site pan antibodies, such as by using non-branched peptide-linked resins.

Common ACE Single-Domain Antibodies.

The ACE monoclonal antibody or VHH fragment consists of a single monomeric variable antibody domain with a molecular weight of 12-15 kDa. This type of antibodies can be made from heavy-chain antibodies found in camelids or cartilaginous fishes, or by splitting the dimeric variable domains from common immunoglobulin G (IgG) from humans or mice into monomers. Single-domain camelids antibodies have been shown to be just as specific as a regular antibody and in some cases they are more robust. They can be easily isolated using the same phage panning procedure used for traditional antibodies. This type of antibodies is heat-resistant, stable towards detergents and high concentrations of urea, and more soluble in water owing to their complementarity determining region 3 (CDR3). Furthermore, the CDR3 structure may facilitate this type of antibodies to reach hidden antigens such as polymeric conjugation sites that are not accessible by regular antibodies or immunoglobulins. This type antibodies can be obtained by immunization of dromedaries, camels, llamas, alpacas or sharks with the common ACE antigen and subsequent isolation of the mRNA coding for heavy-chain antibodies. By reverse transcription and polymerase chain reaction, a gene library of single-domain antibodies containing several million clones is produced. Screening techniques help to identify the clones binding the common ACE antigen. A different method uses naïve gene libraries that usually contain only antibodies with low affinity to the desired antigen, making it necessary to apply affinity maturation by random mutagenesis as an additional step. When the most potent clones have been identified, their DNA sequence can be optimized. The final step is the translation of the optimized single-domain antibody in E. coli, Saccharomyces cerevisiae or other suitable organisms.

Common ACE Recombinant Antibodies:

The common ACE monoclonal antibodies may be natural or artificial (either partially or wholly), for example, made with recombinant DNA methods. Recombinant monoclonal antibody involves molecular cloning and expression of immunoglobulin gene segments in cells, viruses or yeasts. Immunoglobulin DNA expression vectors can be made with the DNAs from hybridoma cells immunized with the common ACE antigen. These vectors can then be transfected into a host cells including, but not limited to, myeloma cells in which recombinant monoclonal antibodies are expressed.

Common ACE Binding Partners or Fusion Proteins:

The ACE antibodies or binding partners may also be made by methods including, but not limited to, phage display, yeast display, ribosome display, bacterial display, and mRNA display.

ACE Humanized Antibodies:

The ACE antigen can be used to make humanized antibodies or human antibodies made by recombinant methods. One approach is to merge an animal DNA sequence that encodes the small binding portion of a monoclonal antibody, with a human DNA sequence that encodes the rest of the large portion of the antibody. The hybrid DNA construct encoding the hybrid antibodies to ACE antigens can be readily isolated, sequenced and expressed for antibody production.

Examples of the common ACE antibodies are provided in FIGS. 5-7

Methods of Ace Exposure, Detection and Isolation

The inventive ACE methods can solve the issues inherited in those epitopes that are: (i) hidden/concealed within molecule(s)/structure(s) and thus poorly or not accessible to large proteins/molecules like antibodies; (ii) poorly antigenic; and (iii) interfered with non-specific bindings. Such epitopes include, but are not limited to, those that are folded within their parent proteins/molecules, macromolecule-to-macromolecule covalent conjugation sites, molecule-to-molecule non-covalent binding sites, proteins/molecules that are inserted into cellular membranes, structures or organelles, and proteins/molecules that are interfered with non-specific bindings. In addition, the ACE structures with free terminals are more charged, and thus more antigenic than the internal sequence (Clark et al., 1969). Therefore, the ACE methods are effective in detecting hidden epitopes as shown in FIGS. 1-7.

In one embodiment, the invention provides methods of artificially, specifically and precisely creating and/or exposing common ACE structures for detection or isolation; thus improving the ACE antigenicity and antibody accessibility in any types of samples or sample preparations, wherein the ACE structures in samples or sample preparations are naturally absent or hidden, and thus, must be artificially and precisely created and/or exposed either in samples or sample preparations by specifically selected hydrolytic enzymes or agents; wherein the artificially creating and/or exposing the ACE structures can be carried out in any type of sample preparations including, but not limited to, in vivo or in vitro, in whole or part of biological bodies or organisms, in isolated organs or organelles, in tissues or tissue sections (with or without fixation), in isolated or cultured cells, in body fluids or cell culture media, in tissue or cell lysates, in cellular or subcellular fractions, on Western blot membranes, in chromatographic or centrifuge fractions, in biochemical assay mixtures, and the like.

The method of creating and exposing the ACE structure in a sample or sample preparation further comprises treating the sample preparation with cross-linkers or fixatives before treating the sample preparation with hydrolytic enzyme or hydrolytic agent. The role of cross-linkers and fixatives is to keep ACE antigens in the samples or sample preparations after hydrolysis so that they will not be moved during analysis. Cross-linkers and fixatives can be selected from any cross-link, adhesion, covalent or noncovalent conjugating chemicals including, but not limited to: chemical cross-linking agents such as the imidoester crosslinker dimethyl suberimidate, the N-hydroxysuccinimide-ester crosslinker BS3 and formaldehyde, the zero-length carbodiimide crosslinker EDC, SMCC or its water-soluble analog, Sulfo-SMCC, and the like. Fixatives also include aldehyde such as formaldehyde, paraformaldehyde, and glutaraldehyde, alcohol, acetone, and osmium tetroxide, and the likes.

The hydrolytic enzymes and agents for artificial ACE creation and/or exposure are specific and precise, rather than random or accidental. The enzymes and agents should be mostly the same, but can also be different, with the one(s) used for the ACE antigen design. If the different hydrolytic enzymes or agents are selected, they must not damage the ACE structures for detection.

There are some non-specific methods to improve the accessibility of a hidden epitope such as using detergents (such as Triton X100 or SDS), different pH solutions, or physical measures such as heat to treat sample before performing antibody-based detections. Although these methods may accidentally and non-specifically expose the epitope, but they are principally and profoundly different, relative to the ACE creating and detecting methods. One explanation is that detergent and heat treatments are non-specific, random or accidental, usually cannot break covalent chemical bonds near the conjugation sites or folded molecules. More importantly, these treatments may often damage or destroy (rather than expose) the epitopes. In comparison, the ACE methods employ the ACE antigen to make antibodies and then use residue chemical bond-specific hydrolytic enzyme(s)/agent(s) to artificially, specifically and precisely create and expose the ACE structures for antibody detection. Therefore, the ACE methods not only fully preserve and expose the antigen structure, but also enhance antigenicity of the antigen structure by creating two (for a linear hidden antigen) or three (for a branched conjugation site) antigenic/charged termini.

A number of antigen retrieval (AR) protocols have been published (Shi, 2011). To date, these protocols were solely for immunochemistry (ICC) or immunohistochemistry (IHC), and have been applied predominantly to archival “paraffin blocks” for IHC in diagnostic surgical pathology (Shi, 2011). Many antibody reagent companies also have antigen retrieval protocols on their websites. However, these protocols are not based on the ACE antigen design and detection described in this application, rather, they are based on random accidental AR attempts and/or reversal of protein formaldehyde adducts and cross-links formed in the course of tissue fixation (Kuhlmann and Krischan, 1981). Therefore, these protocols are used solely for IHC or ICC and usually with a low success rate, and have potential to destroy the antigen of interest. Therefore, the effectiveness of these protocols is accidental and unpredictable.

For example, the Abcam's protocol acknowledges that "most formalin-fixed tissue requires an antigen retrieval step before immunohistochemical staining can proceed. This is due to the formation of methylene bridges during fixation, which cross-link proteins and therefore mask antigenic sites." The Ihcworld's protocol (www.ihcworld.com) describes that "the use of enzyme digestion method may destroy some epitopes . . . ". The protocol of R&D (www.rndsystems.com) recognizes that "the disadvantages of enzyme digestion method are the low success rate for restoring immunoreactivity and the potential for destroying both tissue morphology and the antigen of interest." It is also noted in the Millipore's protocol (www.millipore.com) that "the listed (enzyme digestion) procedure is only suggested; no warranty or guarantee of performance of the above procedure is made or implied".

For pathologists and morphologists, "seeing is believing" and most cancers are diagnosed by morphologic methods. O'Leary et al. (2010) and Shi (2011), two pioneers in the AR research, have suggested: "the AR technique is in many ways still in the developing stage. Further development of the AR technique must be based on a better scientific understanding of the molecular mechanisms, which represents the key pathways to improved cell/tissue sample preparation and standardization of IHC in clinical diagnostic applications."

The inventive ACE methods can robustly improve immunolabeling not only for IHC or ICC, but all antibody-based preparations including, but not limited to, in tissues or tissue lysates, cellular or subcellular fractions, Western blot membranes, chromatographic or centrifuge fractions, and the like.

An additional step of the ACE methods requires artificially, specifically and precisely create (terminals) and/or exposure of the ACE structure before detection. At first glance, this seems an additional step in compared with conventional antibody detection methods. However, in practice, this step can breakup non-specific binding molecules, thus reducing non-specific bindings significantly in all antibody-based applications.

Utilities of Ace Methods, Reagents, Antibodies, Immunoassays and Kits

The present invention encompasses various utilities and applications of the ACE methods including, but not limited to: (i) research and discovery (R&D), (ii) diagnosing diseases, monitoring of disease stage and response to treatment, and disease prognosis, (iii) screening of therapeutic agents, (iv) determining conjugation or de-conjugation enzyme and agent activities, (v) detecting hidden antigens that are normally difficult to be detected by general antibody-based methods, (vi) reducing antibody non-specific bindings in all antibody-based methods, (vii) therapeutic applications for treatment of abnormal molecular conjugation or de-conjugation-related diseases, and (viii) bio-materials.

Discovery of Molecular Conjugation Sites and Sequences

In bioreagent or R&D area, ACE methods, reagents, antibodies, immunoassays and kits can be used in all antibody-based applications including but not limited to detect, identify, isolation, locate and characterize macromolecular conjugation sites or hidden antigens including, but not limited to, protein, saccharide, lipid and nucleic acid, or any combination of the above in a sample. The ACE structures can be artificially created and/or exposed directly either in situ or ex situ on Western blot membranes, tissue sections or any other type of biological sample preparations.

ACE methods, antibodies, reagents, immunoassays, and kits can be used directly for all antibody-based separations of conjugation site-specific and any types of hidden ACE structures including, but not limited to, peptides, saccharide, lipid, nucleic acids, or any combination of the above, followed by identification with methods of genomics, proteomics, glycomics, histomics, metabolomics, and the likes.

An example is to separate molecules in a biological sample with 2-dimensional electrophoresis gel, followed by exposing ACE structures with designated hydrolytic enzymes or agents, and then labeling the spots on the gel/blotting membranes with the ACE antibodies. The ACE positive spots on the gel or membrane can be cut, extracted, and identified with any mass spectrometry (MS)-related methods.

Another example is that ACE structures/segments can be captured with the ACE antibodies in a mixture or biological sample lysates, and then detected by any analytical methods. In the MS method, ACE parent macromolecules in a sample may need to be denatured, and then digested with designated hydrolytic enzymes or agents, to artificially, specifically and precisely expose the ACE structures. After isolation from the sample with the corresponding immobilized ACE antibodies, and then elution from antibody, the ACE structures can then be identified by MS-related methods.

A further example is to separate glyco-, lipidated, UBL- and GPI-anchored proteins with the common ACE antibodies to the common portion of the ACE structures in a sample including, but not limited to: (i) ACE antibodies to the common sumoylation ACE structures (see FIGS. 1 and 7), (ii) ACE antibodies recognizing the common N-linked glycoprotein ACE structures [Fuc(alpha1,6)-GlcNAc-asparagine, or GlcNAc-asparagine asparagine] (see FIGS. 2 and 5), (iii) ACE antibodies to the common ADP-ribosylation ACE structures (see FIG. 3); (iv) ACE antibodies to the common GPI structures (see FIG. 4), and (v) ACE antibodies to the common ubiquitination ACE structure (see FIG. 6); and the like. The common ACE structures separated by the common ACE antibody can then be identified by analytical methods including, but not limited to, MS-methods.

An additional example is to identify ACE structures in samples by the method of antibody array-coupled peptide surface liquid extraction. The procedure includes: (i) coat ACE antibodies to surfaces or matrices mostly by covalent means; (ii) treat samples with specifically selected ACE hydrolytic enzymes or agents; (iii) inhibit the hydrolytic enzymes or agents with inhibitors or any other means, or separate the hydrolytic enzymes or agents from the samples by any biochemical means; (iv) incubate ACE segment-containing samples with ACE antibody-coated surfaces or matrices; (v) separate bound from non-bound ACE segments on the surfaces or matrices by washing; (vi) extract bound ACE segments by appropriate liquid including, but not limited to, low pH buffers or organic solvents; (vii) detect ACE segments in the liquid by any analytical means including, but not limited to, liquid chromatography, fluorescent, ultraviolet and visible spectrometry, or any MS-related methods.

Utilities in Enzymatic Activity Assays

There are a number of approaches for measuring enzyme activities associated with discoveries of therapeutic agents. For example, antibody-based immunoassays of protein kinase activities currently represent the largest drug target class screened in high throughput screening (HTS) laboratories, mostly because phospho-specific antibodies are widely available.

Similar to protein phosphorylation, macromolecule-to-macromolecule conjugation also plays a central role virtually in all cellular metabolic processes. However, unlike protein kinase activity assays, there are no macromolecular conjugation site-specific antibodies currently available for assaying macromolecule-to-macromolecule conjugation enzyme activities.

The present invention provides ACE methods, reagents, antibodies, immunoassays and kits for assaying macromolecular conjugation-related enzyme activities, modulators, cofactor, and the regulatory chemicals.

For example, glycosyltransferases are a group of enzymes (EC 2.4) that catalyze transferring saccharide unit from an activated sugar phosphate (known as the "glycosyl donor") to an acceptor molecule. Protein glycosylation belongs to a co-translational and posttranslational modification and is processed in different cellular compartments, particularly in the endoplasmic reticulum (ER) and Golgi apparatus, by glycosyltransferases and glycosidases. Most, if not all, membrane and secretory proteins are glycosylated. The present invention provides ACE methods and conjugation site-specific antibodies for measuring protein glycosylation-related enzymatic activities including, but not limited to, glycosidases, glycosyltransferases, and their modulators, cofactors or pharmacological agents. These antibody-based assays are typically carried out in a system that contains non-glycosylated substrates including, but not limited to, proteins or peptides, activated glycosyl donors (e.g. UDP-glucose, UDP-galaxies, UDP-GlcNAc, UDP-GalNAc, UDP-xylose, UDP-glucuronic acid, GDP-mannose, GDP-fucose, or CMP-sialic acid), ATP regenerating systems, and glycosylation-related enzymes (either natural or recombinant), or glycosylation-related enzyme modulators, cofactors, chemical activators or inhibitors. After the reaction, the glycosylation enzyme activity as reflected by the rate of formation of the glycosylated proteins or glycosylated peptides, can then be determined with the conjugation site-specific ACE antibody.

Another example is to measure ubiquitination and de-ubiquitination enzyme activities and their modulators: Ubiquitin is a highly conserved regulatory 76 amino acid polypeptide found in all eukaryotic cells either free or covalently bound to other proteins. Ubiquitination (or ubiquitylation) is an enzymatic, protein post-translational modification process in which the carboxylic acid terminal glycine of the activated ubiquitin forms an amide bond to the epsilon amine of the lysine in the modified protein. Protein ubiquitination is carried out consecutively by ubiquitin activating enzyme (E1), ubiquitin conjugating enzyme (E2), and ubiquitin ligase (E3) to catalyze conjugation of ubiquitin to a protein. Successive conjugation of activated ubiquitin to the K-48, or K-63 lysine of the previously conjugated ubiquitin form polyubiquitin chains. Polyubiquitin via K48-linkage is generally recognized by the proteasome for degradation, whereas K63-linked polyubiquitin and monomeric ubiquitination is generally thought, at least in part, to function as proteasome-independent processes including but not limited to endocytosis, and regulation of enzymatic or transcriptional activities.

The present invention provides ACE methods, antibodies, reagents, immunoassays and kits for measuring activities of protein ubiquitination-related enzymes including, but not limited to, ubiquitin ligases, ubiquitin hydrolases as well as their modulators, cofactors or chemical agents. The antibody-based assays of ubiquitin ligase activities can typically be carried out in a system that contains ubiquitin and its substrates (including ubiquitin itself), a ubiquitin conjugation enzyme fraction (s) that contains E1, E2 and E3 enzymes, ATP regenerating systems, and ubiquitin-related enzymes (either natural or recombinant), and ubiquitin-related enzyme modulators, cofactors or chemical agents. Ubiquitination-related enzymatic activities can be measured as the rate of formation of the ubiquitin-to-protein/peptide conjugates with their corresponding conjugation site-specific antibodies.

Diagnostic Applications of the ACE Methods, Antibodies, Reagents, Immunoassays and Kits Abnormal macromolecular conjugations occur in many diseases, and can be used as disease-specific biomarkers. However, antibodies to macromolecule-to-macromolecule conjugation sites are difficult to make by the conventional antibody design and detecting methods, because, as described above, most, if not all, macromolecule-to-macromolecule conjugation sites are hidden antigens, and thus they are not currently available. The inventive methods of designing and detecting hidden ACE antigens can therefore be used for disease diagnosis, staging, monitoring progress and treatment, and prognosis.

The presence of positive ubiquitinated aggregates is a common hallmark of neurological and neurodegenerative diseases including, but not limited to, Alzheimer's disease (AD), Parkinson's disease (PD), Huntington's disease (HD), amyotrophic lateral sclerosis (ALS), prion diseases, as well as vascular diseases, diabetes mellitus, and the like. For instance, stroke induces significant increase in ubiquitinated proteins in brain tissue, blood and cerebrospinal fluid (CSF). AD aggregates contain ubiquitin-conjugated beta-amyloid and Tau proteins (Cripps et al., 2008) and AD CSF has "paired helical filaments antigen" (Kudo, 1994; Mehta et al., 1985; Perry et al., 1989). PD aggregates consist of ubiquitin-conjugated alpha-synuclein and/or parkins. HD has ubiquitin-conjugated polyglutamine repeat aggregates. ALS has ubiquitin-conjugated SOD-containing aggregates and TAR DNA binding protein (TDP-43). Prion diseases have ubiquitin-conjugated prion aggregates in the tissue, CSF and sera, but each disease has its own specific ubiquitin-conjugated proteins as indicated above.

Aberrant glycosylation of proteins changes protein function and activities, and thus can lead to diseases or be byproducts/biomarkers of diseases (Durand et al., 2000; Tong et al., 2003; Troyer et al., 2004; Valmu et al., 2006; Saffroy et al., 2007; Arnold et al., 2008; Debruyne et al., 2008; Ressom et al., 2008; Zhao et al., 2008). For instance, the following diseases contain aberrant glycoproteins: I-cell disease, congenital disorders of glycosylation, leukocyte adhesion deficiency type II, hereditary erythroblastic multinuclearity with a positive acidified serum test, and Wiskott-Aldrich syndrome. In addition, some disease cells, including, but not limited to, those in alcoholism and cancers, can produce unique diseased forms of glycoproteins that can be used as biomarkers for disease diagnosis, staging, monitoring treatment, and prognosis.

A classic example is aberrant glycosylation of alpha-fetoprotein (AFP) in cancer cells. AFP is an oncofetal serum protein consisting of 591 amino acids (*Homo sapiens*) and containing only a single asparagine-linked (N-link) polymeric carbohydrate chain (Debruyne et al., 2008). AFP is a major fetal plasma glycoprotein produced in normal embryonic tissues, but its level becomes barely detectable after birth. In hepatocellular carcinoma (HCC) and seminomatous germ-cell tumors, serum AFP is greatly increased. The reappearance of AFP in HCC patient serum is currently being used as a cancer biomarker. However, the use of AFP as a cancer biomarker is severely limited by the fact that its level is also increased in patients with benign liver diseases including but not limited to hepatitis and liver cirrhosis.

There are several glycosylated forms (known as glycoforms hereafter) of AFP. The glycoform specific for hepatocellular carcinoma (HCC) is the one with the alpha (1,6)-fucosylated innermost GlcNAc known as the core-fucosylation, whereas the glycoform in benign liver diseases does not have this core alpha(1,6)-fucosylation.

Therapeutic Applications of the Ace Methods, Antibodies and Reagents

The ACE antibodies of the invention may be useful, for example, in targeting the conjugation sites, for treating macromolecular conjugation- and aggregation-related diseases including, but not limited to neurodegenerative diseases, cancer, vascular diseases, inflammatory diseases, macular degeneration, transplant rejection, multiple sclerosis, stroke, heart diseases, diabetes, infectious diseases and all protein conjugation-related diseases.

The present invention may be relevant to the delivery of ACE antibodies to the target by carriers including, but not limited to, liposomes. This may be done by packing liposomes with conjugation-site-specific antibodies and hydrolytic enzymes including, but not limited to proteases, glycosidases/glycosylases, lipases or phospholipases, nucleases, or cytotoxic agents such as chemotherapeutic agents, toxins, or radioactive isotopes. Review articles about immunoliposome and immunoliposome-mediated delivery can be found in publications (e.g., Pirollo et al., 2008; Brignole et al., 2005; Bendas, 2001; Maruyama, 2000).

The ACE antigen design of the invention may be used for preparations of vaccines to particular diseases including, but not limited to, neurodegenerative diseases, cancers, conformation diseases (e.g. cystic fibrosis, Celiac diseases, and lysosomal storage diseases), vascular diseases, diabetes-related diseases, and aging-related diseases. The vaccines may be preventive or therapeutic.

Bio-Material Applications of the Ace Methods, Antibodies and Reagents

Conjugation site-specific or other linear hidden antigen antibodies may be useful in biomaterial applications, such as making collagen-like biomaterials for tissue repair. Cell-binding sequences and enzyme crosslink sites of collagen-like biomaterials are crucial in creating collagen mimics that can reproduce biological activities of natural collagens. Transglutaminase catalyzes formation of fibronectin-like, and hyaluronic acid and glycosaminoglycans-like, as well as collagen-like biomaterials. These biomaterials are components of the tissue extracellular matrices. Conjugation site-specific ACE antibodies of the invention may be useful in determining covalent crosslink sites of biomaterials.

The ACE methods, reagents, antibodies, and immunoassays can be used to measure hydrolytic enzymes or chemical agent activities in industrial applications including, but not limited to cellulases and esterase activities in the paper industry, hydrolytic enzyme activities in the leather, pigment removal, biodegradable plastic, or bioethanol industries, and the like.

Kits

In another aspect, the present invention provides kits for detecting the ACEs in biological samples. Such kits comprise ACE antibodies, hydrolytic enzymes or agents, and other items including, but not limited to secondary antibodies, enzyme modulators, cofactors, and buffer systems.

REFERENCES CITED

Patent Documents

| | | |
|---|---|---|
| U.S. Pat. No. 9,181,326 | Apr. 4, 2013 | Rush et al. (Analysis of ubiquitinated polypeptides) |
| U.S. Pat. No. 7,491,501 | Feb. 17, 2009 | Wooten et al., (p62 as probe for protein ubiquitination) |
| U.S. Pat. No. 7,223,556 | May 29, 2007 | Zhou et al. (A method for targeting a target polypeptide for ubiquitin-dependent proteolysis) |
| US 20070218069A | Sep. 20, 2007 | Gordon et al. (about Polyubiquitin antibody) |
| US 20070037221 | Feb. 15 2007 | Block et al. (Lectin-based diagnosis of liver cancer) |
| U.S. Pat. No. 7,022,493 | Apr. 4, 2006 | Issakani et al. (Ubiquitin conjugation assays) |
| U.S. Pat. No. 6,911,335 | Jun. 28, 2005 | Kapeller-Libermann et al. |
| U.S. Pat. No. 6,465,199 | Oct. 15, 2002 | Craig et al. (Compositions and methods for monitoring the modification of natural binding partners. This invention instead encompasses the use of FRET or other detection procedures to monitor the association of polypeptides). |
| U.S. Pat. No. 4,626,507 | Dec. 2, 1986 | Trowbridge et al. (Monoclonal antibody to a glycoprotein, but not specific to the glycosylation site) |
| U.S. Pat. No. 7,460,960 | Mar. 17, 2009 | Lee et al., Proteome epitope tags and methods of use thereof in protein modification analysis |
| WO 02/25287 | Mar. 4, 2003 | Soloviev et al., Detection of Peptide |
| U.S. Pat. No. 5,972,623 | Oct. 14, 1999 | Krane et al., Collagen-peptide assay method |
| U.S. Pat. No. 7,803,553 | Sep. 28, 2010 | Kojima et al., Methods of use of antibodies which recognize a protease cleavage site of an LAP fragment of TGF-β |
| U.S. Pat. No. 6,762,045 | Mar. 20, 2002 | Membrane derived caspase-3, compositions comprising the same and methods of use therefor |

OTHER REFERENCES

Arnold J N, Saldova R, Hamid U M, Rudd P M (2008) Evaluation of the serum N-linked glycome for the diagnosis of cancer and chronic inflammation. Proteomics. 8:3284-3293.

Bendas G (2001) Immunoliposomes: A Promising Approach to Targeting Cancer Therapy. BioDrugs. 15:215-224.

Brignole C, Marimpietri D, Pagnan G, Di Paolo D, Zancolli M, Pistoia V, Ponzoni M, Pastorino F (2005) Neuroblastoma targeting by c-myb-selective antisense oligonucleotides entrapped in anti-GD2 immunoliposome: immune cell-mediated anti-tumor activities. Cancer Lett. 228:181-6.

Clark L G, Maurer P H (1969) Antigenicity of polypeptides (poly-alpha-amino acids). Immunological reactions of sheep antisera to a polymer of glutamic acid, alanine and tyrosine. Int Arch Allergy Appl Immunol. 35:58-64.

Cripps D, Thomas S N, Jeng Y, Yang F, Davies P, Yang A J (2008) Alzheimer disease-specific conformation of hyperphosphorylated paired helical filament-Tau is polyubiquitinated through Lys-48, Lys-11, and Lys-6 ubiquitin conjugation. J Biol Chem. 281:10825-38.

Daniels C M, Ong S E, Leung A K (2015) The Promise of Proteomics for the Study of ADP-Ribosylation. Mol Cell. 58:911-24.

Debruyne E N, Delanghe J R (2008) Diagnosing and monitoring hepatocellular carcinoma with alpha-fetoprotein: new aspects and applications. Clin Chim Acta. 395:19-26.

Denis N J, Vasilescu J, Lambert J P, Smith J C, Figeys D (2007) Tryptic digestion of ubiquitin standards reveals an improved strategy for identifying ubiquitinated proteins by mass spectrometry. Proteomics. 7:868-874.

Dohm C P, Kermer P, Bähr M (2008) Aggregopathy in neurodegenerative diseases: mechanisms and therapeutic implication. Neurodegener Dis. 5:321-38.

Durand G, Seta N (2000) Protein glycosylation and diseases: blood and urinary oligosaccharides as markers for diagnosis and therapeutic monitoring. Clin Chem. 46:795-805.

Fujimuro M, Yokosawa H (2005) Production of antipolyubiquitin monoclonal antibodies and their use for characterization and isolation of polyubiquitinated proteins. Methods Enzymol. 399:75-86.

Gagné J P, Bonicalzi M E, Gagné P, Ouellet M E, Hendzel M J, Poirier G G (2005) Poly(ADP-ribose) glycohydrolase is a component of the FMRP-associated messenger ribonucleoparticles. Biochem J. 392:499-509.

Hu P, Shi B, Geng F, Zhang C, Wu W, Wu X Z (2008) E-cadherin core fucosylation regulates nuclear beta-catenin accumulation in lung cancer cells. Glycoconj J. 25:843-850.

Kim W, Bennett E J, Huttlin E L, Guo A, Li J, Possemato A, Sowa M E, Rad R, Rush J, Comb M J, Harper J W, Gygi S P (2010) Systematic and quantitative assessment of the ubiquitin-modified proteome. Mol Cell. 44:325-240.

Kossowska B, Ferens-Sieczkowska M, Gancarz R, Passowicz-Muszyńska E, Jankowska R (2005) Fucosylation of serum glycoproteins in lung cancer patients. Clin Chem Lab Med. 43:361-9.

Kudo T, Iqbal K, Ravid R, Swaab D F, Grundke-Iqbal I (1994) Alzheimer disease: correlation of cerebro-spinal fluid and brain ubiquitin levels. Brain Res. 639:1-7.

Kuhlmann W D, Krischan R (1981) Resin embedment of organs and postembedment localization of antigens by immunoperoxidase methods. Histochemistry. 72:377-89.

Laing S, Koch-Nolte F, Haag F, Buck F (2011) Strategies for the identification of arginine ADP-ribosylation sites. J. Proteomics. 75:169-176.

Mai S, Garini Y (2006) The significance of telomeric aggregates in the interphase nuclei of tumor cells. J Cell Biochem. 97:904-915.

Maruyama K (2000) In vivo targeting by liposomes. Biol Pharm Bull. 23:791-9.

Matsumoto M L, Wertz I E, Kirkpatrick D S, Lill J R, Tan J, Dugger D, Gordon N, Sidhu S S, Fellouse F A, Komuves L, French D M, Ferrando R E, Lam C, Compaan D, Yu C, Bosanac I, Hymowitz S G, Kelley R F, Dixit V M. (2008) Ubiquitin chain editing revealed by polyubiquitin linkage-specific antibodies. Cell. 134:668-78.

Meerwaldt R, van der Vaart M G, van Dam G M, Tio R A, Hillebrands J L, Smit A J, Zeebregts C J (2008) Clinical relevance of advanced glycation endproducts for vascular surgery. Eur J Vasc Endovasc Surg. 36:125-31.

Mehta A, Block T M (2008) Fucosylated glycoproteins as markers of liver disease. Dis Markers. 25:259-65.

Mehta P D, Thal L, Wisniewski H M, Grundke-Iqbal I, Iqbal K (1985) Paired helical filament antigen in CSF. Lancet. 2:35.

Miyoshi E, Shinzaki S, Moriwaki K, Matsumoto H (2010) Identification of fucosylated haptoglobin as a novel tumor marker for pancreatic cancer and its possible application for a clinical diagnostic test. Methods Enzymol. 478:153-64.

Moriwaki K, Miyoshi E (2010) Fucosylation and gastrointestinal cancer. World J Hepatol. 2:151-61.

Narisada M, Kawamoto S, Kuwamoto K, Moriwaki K, Nakagawa T, Matsumoto H, Asahi M, Koyama N, Miyoshi E (2008) Identification of an inducible factor secreted by pancreatic cancer cell lines that stimulates the production of fucosylated haptoglobin in hepatoma cells. Biochem Biophys Res Commun. 377:792-796.

O'Leary T J, Fowler C B, Evers D L, Cunningham R E, Mason J T (2010) Commentary: future directions. In: Shi S-R, Taylor C R, editors. Antigen retrieval immunohistochemistry based research and diagnostics. Hoboken (N.J.): John Wiley. p. 323-331.

Osumi D, Takahashi M, Miyoshi E, Yokoe S, Lee S H, Noda K, Nakamori S, Gu J, Ikeda Y, Kuroki Y, Sengoku K, Ishikawa M, Taniguchi N (2009) Core fucosylation of E-cadherin enhances cell-cell adhesion in human colon carcinoma WiDr cells. Cancer Sci. 100:888-95.

Otake Y, Fujimoto I, Tanaka F, Nakagawa T, Ikeda T, Menon K K, Hase S, Wada H, Ikenaka K (2001) Isolation and characterization of an N-linked oligosaccharide that is significantly increased in sera from patients with non-small cell lung cancer. J Biochem. 129:537-42.

Peng J, Schwartz D, Elias J E, Thoreen C C, Cheng D, Marsischky G, Roelofs J, Finley D and Gygi S P (2003) A proteomics approach to understanding protein ubiquitination. Nat Biotechnol. 21:921-926.

Perry G, Mulvihill P, Fried V A, Smith H T, Grundke-Iqbal I, Iqbal K (1989) Immunochemical properties of ubiquitin conjugates in the paired helical filaments of Alzheimer disease. J Neurochem. 52:1523-8.

Pirim I (1998) Production of anti-polyubiquitin and anti-ubiquitin carboxyl terminal hydrolase antibodies and immunohistochemically assessment of them on brain sections of Alzheimer's disease and Lewy body disease. Int J Neurosci. 95:33-42.

Pirollo K F, Chang E H (2008) Targeted delivery of small interfering RNA: approaching effective cancer therapies. Cancer Res. 68:1247-50.

Ressom H W, Varghese R S, Goldman L, An Y, Loffredo C A, Abdel-Hamid M, Kyselova Z, Mechref Y, Novotny M, Drake S K, Goldman R (2008) Analysis of MALDI-TOF mass spectrometry data for discovery of peptide and glycan biomarkers of hepatocellular carcinoma. J Proteome Res. 7:603-10.

Saffroy R, Pham P, Reffas M, Takka M, Lemoine A, Debuire B (2007) New perspectives and strategy research biomarkers for hepatocellular carcinoma. Clin Chem Lab Med. 45:1169-1179.

Saldova R, Fan Y, Fitzpatrick J M, Watson R W, Rudd P M (2010) Core fucosylation and {alpha}2-3 sialylation in serum N-glycome is significantly increased in prostate cancer comparing to benign prostate hyperplasia. Glycobiology. 21:195-205

Shi S R, Shi Y, Taylor C R (2011) Antigen retrieval immunohistochemistry: review and future prospects in research and diagnosis over two decades. J Histochem Cytochem. 59:13-32.

Thornalley P J (2002) Glycation in diabetic neuropathy: characteristics, consequences, causes, and therapeutic options. Int Rev Neurobiol. 50:37-57.

Tong L, Baskaran G, Jones M B, Rhee J K, Yarema K J (2003) Glycosylation changes as markers for the diagnosis and treatment of human disease. Biotechnol Genet Eng Rev. 20:199-244.

Troyer D A, Mubiru J, Leach R J, Naylor S L (2004) Promise and challenge: Markers of prostate cancer detection, diagnosis and prognosis. Dis Markers. 20:117-128

Valmu L, Alfthan H, Hotakainen K, Birken S, Stenman U H (2006) Site-specific glycan analysis of human chorionic gonadotropin beta-subunit from malignancies and pregnancy by liquid chromatography--electrospray mass spectrometry. Glycobiology. 16:1207-18.

Ward R (2002) Antibody phage display. Immunology and Cell Biology. 80:316-317,

Wu L H, Shi B Z, Zhao Q L, Wu X Z (2010) Fucosylated glycan inhibition of human hepatocellular carcinoma cell migration through binding to chemokine receptors. Glycobiology. 20:215-23.

Xu G, Paige J S and Jaffrey S R (2010) Global analysis of lysine ubiquitination by ubiquitin remnant immunoaffinity profiling. Nat Biotechnol. 28:868-73.

Young L S, Gascon R, Alam S, Bermudez L E (1989) Monoclonal antibodies for treatment of gram-negative infections. Rev Infect Dis. Suppl 7:S1564-71.

Zamze S E, Ferguson M A, Collins R, Dwek R A, Rademacher T W (1988) Characterization of the cross-reacting determinant (CRD) of the glycosyl-phosphatidylinositol membrane anchor of Trypanosoma brucei variant surface glycoprotein. Eur J Biochem. 176:527-534.

Zhang Y, Wang J, Ding M, Yu Y (2013) Site-specific characterization of the Asp- and Glu-ADP-ribosylated proteome. Nat. Methods. 10:981-984

Zhao J, Patwa T H, Lubman D M, Simeone D M (2008) Protein biomarkers in cancer: natural glycoprotein microarray approaches. Curr Opin Mol Ther. 10:602-610.

We claim:

1. A method of antibody binding to at least one Artificially Cleaved Epitope (ACE) structure in a biological sample, wherein the ACE structure in its intact or natural form in the sample is either less antigenic or hidden and thus poorly recognizable by the antibody, and wherein the ACE structure is artificially created for the antibody binding, comprising steps of:
    (i) Designing a hydrolytic enzyme or hydrolytic agent cleaved macromolecule-to-macromolecule conjugation site specific ACE structure of formula Ln---L2-L1(-S1-S2---Sm)-L1'-L2'---Lm' or Ln---L2-L1-L1'-L2'---Lm(-S1-S2---Sm)' wherein the ACE structure consists of a first oligomer having the sequence Ln---L2-L1-L1'-L2'---Lm', and a second oligomer having the sequence S1-S2---Sm; wherein the second oligomer is covalently conjugated to L1 or Lm' via S1; wherein at least one of Ln, Lm' and Sm residues is a free terminal that is artificially created via chemical bond-specific cleavage by at least one hydrolytic enzyme or hydrolytic agent;
    (ii) Chemically synthesizing the ACE structure described in step (i) and isolating the ACE structure;
    (iii) Producing an antibody against the isolated ACE structure of step (ii), wherein the antibody specifically binds the ACE structure;
    (iv) Creating the ACE structure in the sample by treating the sample with the same hydrolytic enzyme or hydrolytic agent that is/are being used to create the free terminal(s) in step (i), thereby exposing the formerly hidden ACE structure in the sample to specific interaction with the antibody; and
    (v) Capturing, isolating, or detecting the ACE structure created in step (iv) in the sample with the antibody or a matrix coated with the antibody.

2. The method of claim 1 wherein the hydrolytic enzyme is selected from the group consisting of a glycosidase, a lipase, a phospholipase, a nuclease, a protease, a polyribosyl hydrolase, and combinations thereof.

3. The method of claim 1 wherein the hydrolytic agent is a substance with chemical bond-specific hydrolysis activity, and is selected from the group consisting of cyanogen bromide (CNBr), 2-nitro-5-thiocyanobenzoic acid, BNPSskatole, formic acid, and or combinations thereof.

4. The method of claim 1 wherein the first oligomer of the ACE structure contains 1 to 200 residues, and the second oligomer contains 1 to 50 residues.

5. The method of claim 1 wherein the antibody is a polyclonal antibody, a monoclonal antibody, a bi- or multi-specific antibody, a recombinant antibody, a single-domain antibody, a heavy-chain ($V_H$H fragment) antibody, an antibody fragment, a humanized antibody, a binding partner, or an antibody-like molecule.

6. The method of claim 1 wherein the ACE structure is selected from the group consisting of a saccharide-to-protein segment, a phosphotidylethanolamine-to-protein or ethanolamine-to-protein segment, a lipid-to-protein segment, a phospholipid-to-protein segment, a fatty acid-to-protein segment, a GPI-to-protein segment, a UBL-to-protein segment, a ubiquitin-to-protein segment, and an (ADP-ribose)-to-protein segment.

7. The method of claim 6 wherein the protein-to-UBL segment is a protein-to-SUMO/Sentrin/Smt3 segment, a protein-to-NEDD8/Rub1 segment, a protein-to-ISG15 segment, a protein-to-FAT10 segment, a protein-to-URM1 segment, a protein-to-FUB1 segment, a protein-to-MUB segment, a protein-to-UFM1 segment, a protein-to-ATG8/LC3 segment, a protein-to-ATG12 segment, or a protein-to-UBL5/Hub1 segment.

8. The method of claim 1 wherein an example of the ACE structure in step (i) is a saccharide-to-protein conjugation site-specific segment, wherein L1 is an asparagine residue (N), L1' is any amino acid, and L2' is either a serine or threonine (S/T), wherein the second oligomer consists of either one saccharide N-acetyl-D-glucosamine (GlcNAc) residue or two saccharide (fucosylated GlcNAc=GlcNAc-Fuc) residues, and wherein GlcNAc or GlcNAc-Fuc is covalently conjugated to L1 (N) residue.

9. The method of claim 8 wherein the antibody binds the common residues of the ACE structure: -N-(GlcNAc)- or -N-(GlcNAc-Fuc)-, or -N-(GlcNAc)-L1'-S/T- or -N-(GlcNAc-Fuc)-L1'-S/T-, and wherein the antibody binding is independent of the other L residues of the ACE structure.

10. The method of claim 1 wherein capturing, isolating, or detecting the ACE structure in step (v) is performed by a antibody-based method selected from the group consisting of enzyme-linked immunosorbent assay (ELISA), Western blotting, immunoprecipitation (IP), immunoaffinity isolation, enzyme linked immunospot (ELISPOT), immunostaining, immunolabeling, immunohistochemistry, immunocytochemistry, flow cytometry, affinity chromatography, mass spectrometry, multiplex assay, and combinations thereof.

11. The method of claim 1 wherein step (ii) further comprises treating the ACE structure with a chemical cross-linker or fixative selected from the group consisting of an aldehyde, an alcohol, acetone, and osmium tetroxide for some antibody-based applications.

* * * * *